United States Patent
DeFelippis et al.

(10) Patent No.: US 7,238,663 B2
(45) Date of Patent: Jul. 3, 2007

(54) PRE-MIXES OF GLP-1 AND BASAL INSULIN

(75) Inventors: Michael Rosario DeFelippis, Carmel, IN (US); Richard Dennis DiMarchi, Carmel, IN (US); Kingman Ng, Carmel, IN (US)

(73) Assignee: Eli Lilly and Company, Indianapolis, IN (US)

( * ) Notice: Subject to any disclaimer, the term of this patent is extended or adjusted under 35 U.S.C. 154(b) by 415 days.

(21) Appl. No.: 10/486,333

(22) PCT Filed: Aug. 23, 2002

(86) PCT No.: PCT/US02/21856

§ 371 (c)(1), (2), (4) Date: Feb. 9, 2004

(87) PCT Pub. No.: WO03/020201

PCT Pub. Date: Mar. 13, 2003

(65) Prior Publication Data

US 2004/0235710 A1 Nov. 25, 2004

Related U.S. Application Data

(60) Provisional application No. 60/386,061, filed on Jun. 4, 2002, provisional application No. 60/385,266, filed on May 31, 2002, provisional application No. 60/315,460, filed on Aug. 28, 2001.

(51) Int. Cl.
*A61K 38/00* (2006.01)

(52) U.S. Cl. .......................................... 514/12; 514/3

(58) Field of Classification Search ............ 514/12, 514/3
See application file for complete search history.

(56) References Cited

U.S. PATENT DOCUMENTS

| | | | |
|---|---|---|---|
| 5,118,666 A | 6/1992 | Habener | |
| 5,120,712 A | 6/1992 | Habener | |
| 5,461,031 A | 10/1995 | De Felippis | |
| 5,512,549 A | 4/1996 | Chen et al. | |
| 5,514,646 A | 5/1996 | Chance et al. | |
| 5,545,618 A | 8/1996 | Buckley et al. | |
| 5,547,929 A | 8/1996 | Anderson, Jr. et al. | |
| 5,650,486 A | 7/1997 | De Felippis | |
| 5,656,722 A | 8/1997 | Dorschug | |
| 5,705,483 A | 1/1998 | Galloway et al. | |
| 5,747,642 A | 5/1998 | De Felippis | |
| 5,840,680 A | 11/1998 | Balschmidt | |
| 5,977,071 A | 11/1999 | Galloway et al. | |
| 6,011,007 A | 1/2000 | Havelund et al. | |
| 6,133,235 A | 10/2000 | Galloway et al. | |
| 6,191,102 B1 | 2/2001 | DiMarchi et al. | |
| 6,221,633 B1 | 4/2001 | Ertl et al. | |
| 6,221,837 B1 | 4/2001 | Ertl et al. | |
| 6,268,335 B1 * | 7/2001 | Brader | 514/3 |
| 6,268,343 B1 | 7/2001 | Knudsen et al. | |
| 6,277,877 B1 | 8/2001 | Hoover et al. | |
| 6,875,741 B2 | 4/2005 | Pillutla et al. | |
| 2001/0047084 A1 | 11/2001 | Knudsen et al. | |
| 2003/0224983 A1 * | 12/2003 | Nielsen | 514/12 |
| 2003/0236190 A1 * | 12/2003 | Pillutla et al. | 514/12 |

FOREIGN PATENT DOCUMENTS

| | | |
|---|---|---|
| WO | WO 95/07931 | 3/1995 |
| WO | WO 95/31214 | 11/1995 |
| WO | WO 99/07404 | 2/1999 |
| WO | WO 99/25727 | 5/1999 |
| WO | WO 99/25728 | 5/1999 |
| WO | WO 99/32116 | 7/1999 |
| WO | WO 99/43708 | 9/1999 |
| WO | WO 00/37098 | 6/2000 |
| WO | WO 00/66629 | 11/2000 |
| WO | WO 03/053339 | 7/2003 |

OTHER PUBLICATIONS

Adelhorst, et al., "Structure-Activity Studies of Glucagon-Like Peptide-1." 1994, J. Biological Chemistry vol. 269: 6275-6278.
Brange, "Galenics of Insulin: The Physico-chemical and Pharmaceutical Aspects of Insulin and Insulin Preparation." 1987.
Markussen, et al., "Soluble, Prolonged-acting Insulin Derivatives. III. Degree of Protraction, Crystallizability and Chemical Stability of Insulins Substituted in Positions A21, B13, B23, B27 and B30." Protein Eng. 1988, vol. 2: p. 157-166.
Markussen, et al., "Soluble, Fatty Acid Acylated Insulins Bind to Albumin and Show Protracted Action in Pigs." Diabetologia, 1996, vol. 39, pp. 281-288.
Myers, et al., "Acylation of Human Insulin With Palmitic Acid Extends the Time Action of Human Insulin in Diabetic Dogs." Diabetes, 1997, vol. 46, pp. 637-642.
Vella, et al., "Effect of Glucagon-Like Peptide 1 (7-36) Amide on Glucose Effectiveness and Insulin Action in People With Type 2 Diabetes." Diabetes, Apr. 2000, vol. 49, pp. 611-617.
Zander, et al., "Additive Glucose-Lowering Effects of Glucagon-Like Peptide-1 and Metformin in Type 2 Diabetes." Apr. 2001, vol. 24, No. 4, pp. 720-725.
U.S. Appl. No. 09/538,038, Mar. 29, 2000, ABD'd.
U.S. Appl. No. 09/146,127, Sep. 2, 1998, ABD'd.

* cited by examiner

*Primary Examiner*—Cecilia J. Tsang
*Assistant Examiner*—Maury Audet
(74) *Attorney, Agent, or Firm*—Alejandro Martinez; Gregory A. Cox

(57) ABSTRACT

The present invention encompasses pre-mixed formulations comprising a GLP-1 polypeptide and a basal insulin.

3 Claims, 2 Drawing Sheets

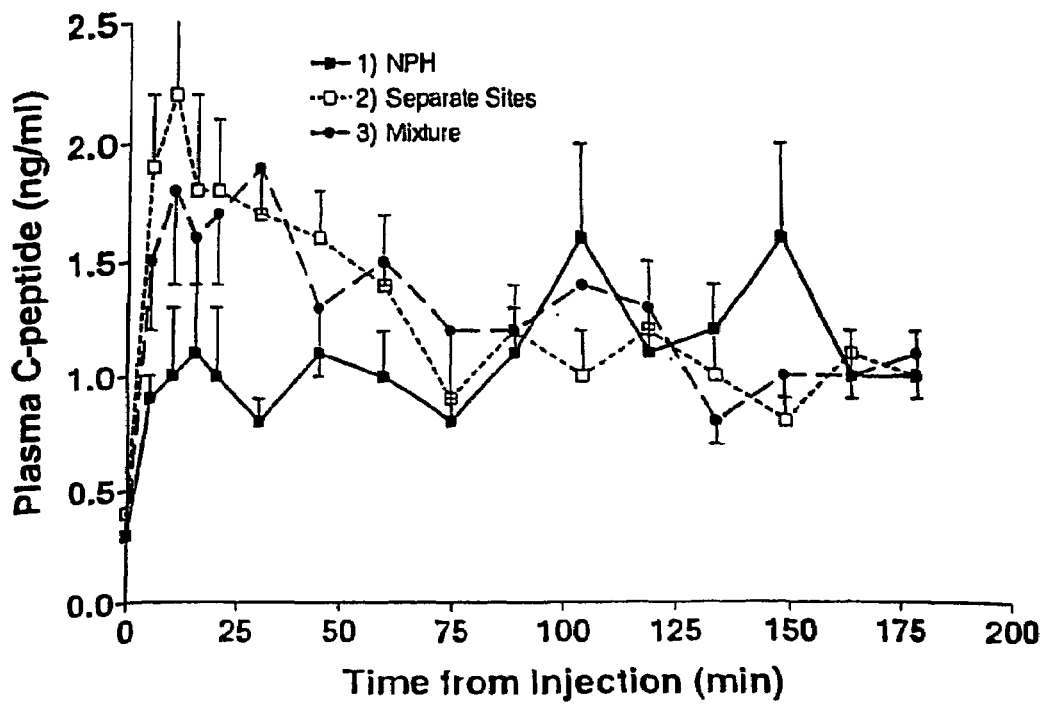
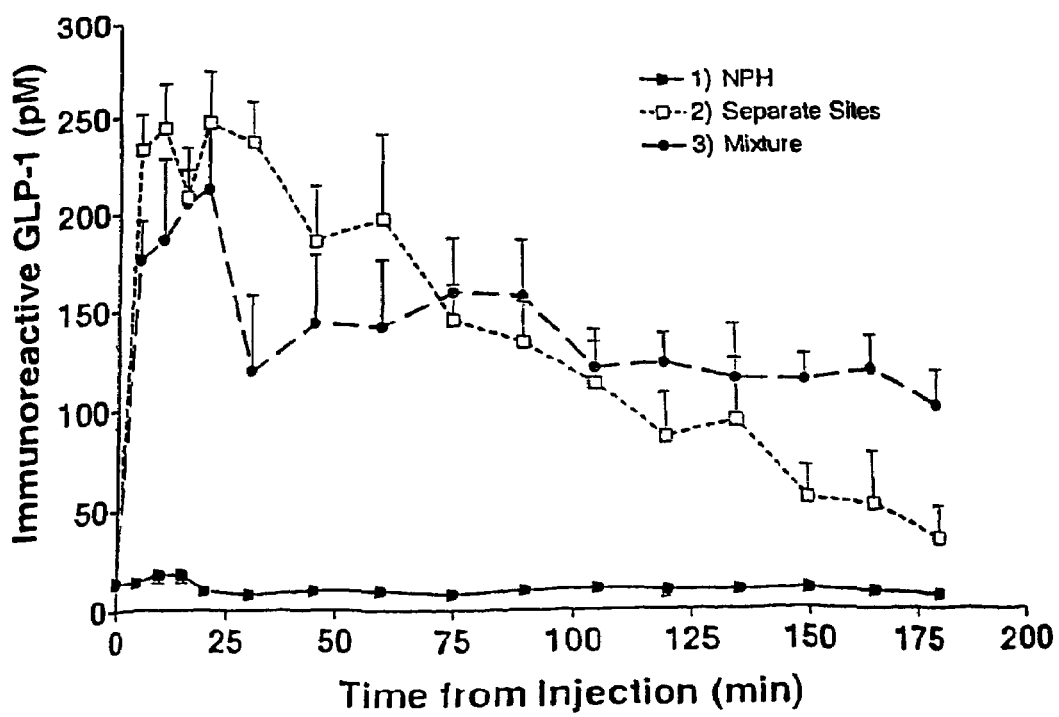

PRE-MIXES OF GLP-1 AND BASAL INSULIN

This is the national phase application, under 35 USC 371, for PCT/US02/21856, filed Aug. 23, 2002, which claims the priority of U.S. provisional application Nos. 60/386,061, filed Jun. 4, 2002, 60/385,266, filed May 31, 2002, and 60/315,460, filed Aug. 28, 2001.

The present invention relates to pre-mixed formulations of a glucagon like peptide and a basal insulin. These pre-mixed formulations can be used to treat diseases such as non-insulin dependent diabetes mellitus and insulin dependent diabetes mellitus.

It has long been the goal of diabetes therapy to administer drugs that result in a pattern of insulin secretion that mimics the pattern of endogenous insulin secretion in normal individuals. The daily physiological demand for insulin fluctuates and can be separated into two phases: (a) the absorptive phase requiring a pulse of insulin to dispose of the meal-related blood glucose surge, and (b) the post absorptive phase requiring a sustained delivery of insulin to regulate hepatic glucose output for maintaining optimal fasting blood glucose.

Once oral agents fail to adequately control blood glucose in type 2 diabetics, it becomes extremely important to achieve near normal glycemic control and thereby minimize the complications associated with diabetes. When oral agents fail, the only alternative is to treat patients with insulin that must be dosed and timed with respect to meal-related glucose excursions and hepatic glucose output during periods of fasting so as to effectively normalize glucose without causing hypoglycemia. Control of the first phase involving disposal of the meal-related blood glucose surge is often the most difficult to achieve without producing side effects such as hypoglycemia. This is because the dose of medications must be timed such that blood insulin levels peak when glucose levels surge after a meal. For example, if insulin-inducing medication is taken too long before a meal there is a substantial risk of hypoglycemia which can result in a coma or even death. Furthermore, if the medication is taken too long after a meal then blood glucose levels will remain high after a meal, which over a period of time can cause severe complications.

Various commercially available insulin formulations with different time actions have been developed. However, it is often quite difficult for a type 2 patient to transition from a treatment involving oral medications to one involving injections of insulin that must be carefully timed with meals to avoid complications such as hypoglycemia. Thus, there is a need for a convenient therapy that adequately treats this intermediate stage of type 2 diabetes with a reduced risk of hypoglycemia.

Glucagon-like peptide-1 (GLP-1) shows great promise as a treatment for type 2 diabetes especially for those patients no longer able to control blood glucose with oral medications. GLP-1 has a variety of physiologically significant activities. For example, GLP-1 has been shown to stimulate insulin release, lower glucagon secretion, inhibit gastric emptying, and enhance glucose utilization. [Nauck, M. A., et al., (1993) *Diabetologia* 36:741-744; Gutniak, M., et al., (1992) *New England J. of Med.* 326:1316-1322; Nauck, M. A., et al., (1993) *J. Clin. Invest.* 91:301-307]. Furthermore, some animals studies suggest that GLP-1 may actually preserve beta cells, inhibit beta cell apoptosis, and induce beta cell proliferation. One of the most exciting observations is that GLP-1 activity is controlled by blood glucose levels. When levels drop to a certain threshold level, GLP-1 is not active. Thus, there is no risk of hypoglycemia associated with treatment involving GLP-1.

However, the usefulness of a monotherapy involving GLP-1 peptides has been limited by their fast clearance and short half-lives. Although numerous analogs and derivatives have been developed with a longer half-life compared to native GLP-1(7-37)OH, the activity profile of these molecules is generally still not sufficient to adequately control fasting glucose levels especially between meals and during the bedtime hours.

The present invention overcomes the problems associated with using relatively-short acting GLP-1 compounds to treat type 2 diabetes as well as the hypoglycemic risk associated with insulin therapy. The present invention encompasses pre-mixed formulations comprising a GLP-1 compound and a basal insulin. The GLP-1 in the mixture normalizes meal-related blood glucose excursions without the risk of hypoglycemia and the basal insulin functions to control fasting blood glucose levels especially during bedtime hours. In addition to providing optimal glycemic control with a reduced risk of hypoglycemia, a treatment regimen that employs the pre-mixed formulations of the present invention is more convenient than treatment with insulin alone in that doses do not need to be timed as carefully with meals because GLP-1 compounds do not cause hypoglycemia.

The combination of GLP-1 and basal insulin as a pre-mixed formulation has not been studied or even suggested. It was not understood until the present invention whether GLP-1 and basal insulin could be formulated together such that both agents are chemically and physically stable and retain the desired time action. The molecular interactions between GLP-1 and insulin could compromise the time action of either agent. Furthermore, the conditions necessary to achieve chemical and physical stability are different for each agent when formulated alone. Until the present invention one skilled in the art would not appreciate that the two agents may be formulated together to achieve optimal glycemic control in a stable, pharmaceutical formulation.

Thus, in the present invention, it was surprising that pre-mixed formulations could be prepared such that the GLP-1 compound and the basal insulin present in the formulation produce a profile of action and physiological response similar to that obtained when the GLP-1 and the basal insulin compounds are injected separately.

In one form thereof, the present invention provides pre-mixed formulations comprising a GLP-1 compound and a basal insulin.

The present invention further provides a process of preparing the pre-mixed formulations, which comprises mixing a GLP-1 compound and a basal insulin in an aqueous solution such that the GLP-1 retains insulinotropic activity while the basal insulin retains a profile of action that is consistent with that produced by treatment with basal insulin alone. Preferably, the pre-mixed formulation is prepared by mixing a stock solution of a GLP-1 compound with a basal insulin at various ratios. Preferably, a pharmaceutically acceptable buffer, a preservative, or an isotonicity agent may be added to the pre-mixed formulation.

The present invention further provides a method of administering an effective amount of a pre-mixed formulation comprising a GLP-1 compound and a basal insulin.

The present invention further provides a method of treating non-insulin dependent diabetes, insulin dependent diabetes, hyperglycemia, obesity, functional dyspepsia, irritable bowel syndrome, catabolic changes after surgery, myocardial infarction, or stroke using the formulations discussed herein.

The present invention further provides use of the formulation for the preparation of a medicament in the treatment of non-insulin dependent diabetes, insulin dependent diabetes, hyperglycemia, obesity, therapeutic reduction of body weight in a human subject, functional dyspepsia, irritable bowel syndrome, catabolic changes after surgery, myocardial infarction, and stroke in a mammal.

FIG. 3 is a graphical representation of the plasma C-peptide concentrations (ng/mL) in dogs following initiation of a 3 hour hyperglycemic clamp at 150 mg/dl and SC administration of $Val^8$-GLP-1/NPH mixture formulation (Mixture), separate $Val^8$-GLP-1 solution and insulin-NPH suspension SC administrations (Separate Sites), or insulin-NPH suspension SC administration (NPH).

FIG. 4 is a graphical representation of the immunoreactive $Val^8$-GLP-1 (PM) in dogs following initiation of a 3 hour hyperglycemic clamp at 150 mg/dl and SC administration of $Val^8$-GLP-1/NPH mixture formulation (Mixture), separate $Val^8$-GLP-1 solution and insulin-NPH suspension SC administrations (Separate Sites), or insulin-NPH suspension SC administration (NPH).

Figure 1:
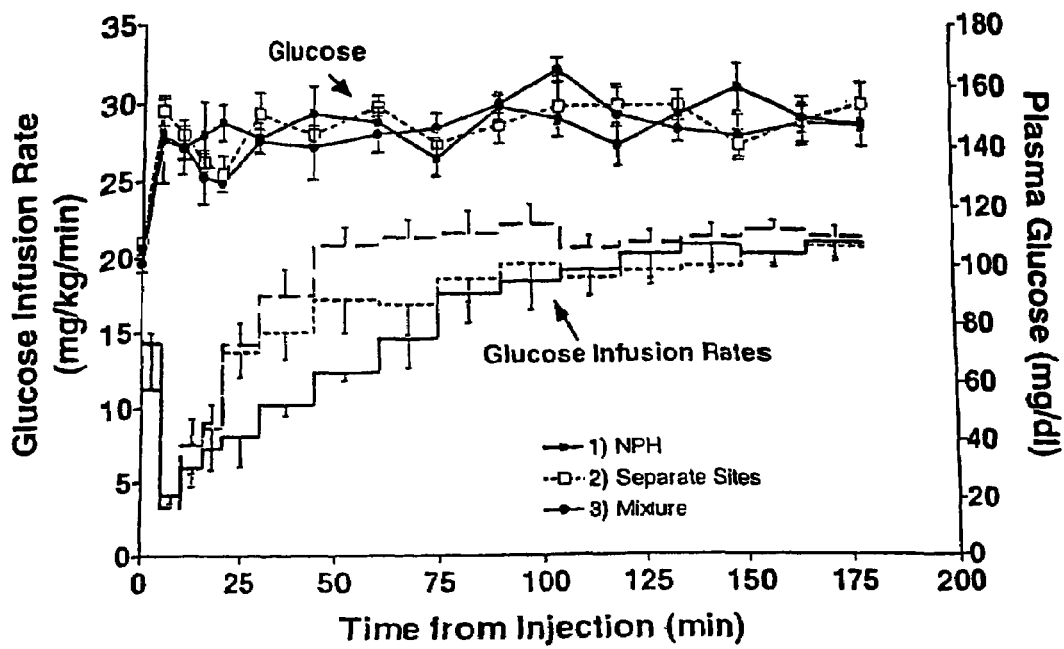
FIG. 1 is a graphical representation of the glucose infusion rates measured in dogs following initiation of a 3 hour hyperglycemic clamp at 150 mg/dl and subcutaneous (SC) administration of $Val^8$-GLP-1/NPH mixture formulation (Mixture), separate $Val^8$-GLP-1 solution and insulin-NPH suspension SC administrations (Separate Sites), or insulin-NPH suspension SC administration (NPH).
Figure 2:
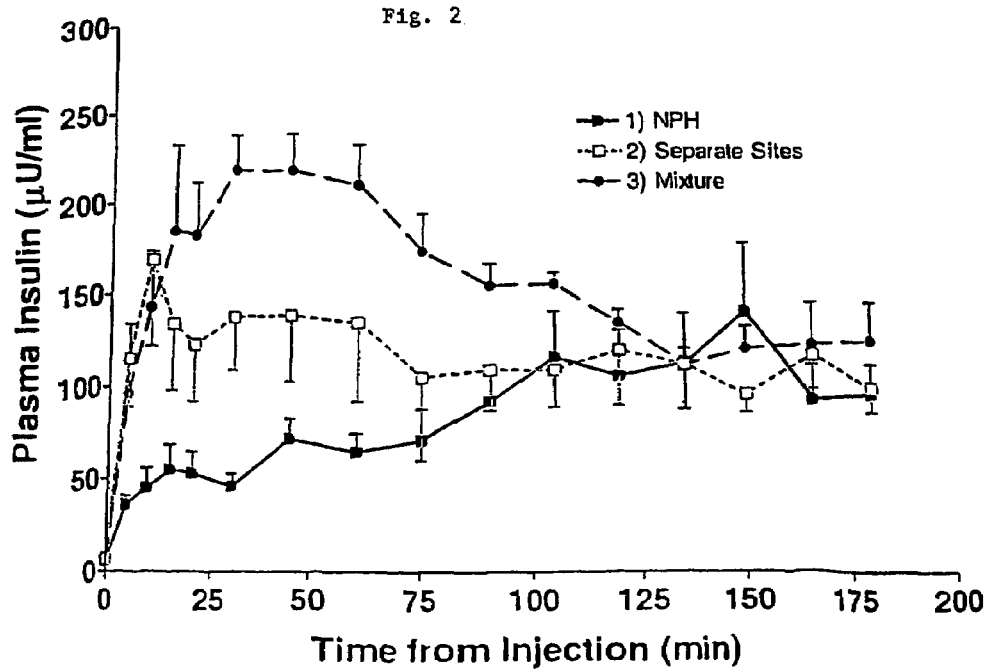
FIG. 2 is a graphical representation of the plasma insulin concentrations (gU/mL) in dogs following initiation of a 3 hour hyperglycemic clamp at 150 mg/dl and SC administration of $Val^8$-GLP-1/NPH mixture formulation (Mixture), separate $Val^8$-GLP-1 solution and insulin-NPH suspension SC administrations (Separate Sites), or insulin-NPH suspension SC administration (NPH).

The three-letter abbreviation code for amino acids used in this specification conforms with the list contained in Table 3 of Annex C, Appendix 2 of the PCT Administrative Instructions and with 37 C.F.R. § 1.822(d)(1)(2000).

The term "pre-mixed formulations" of the present invention refers to biphasic or soluble formulations which comprise a GLP-1 compound and a basal insulin. As is the custom in the art) the N-terminal residue of a GLP-1 compound is represented as position 7. In the nomenclature used herein to describe GLP-1 analogs, the substituting amino acid and its position is indicated prior to the parent structure. For example $Val^8$-GLP-1(7-37)OH designates a GLP-1 analog in which the alanine normally found at position 8 in GLP-1(7-37)OH is replaced with valine.

For purposes of the present invention, the term "GLP-1 compound" as used herein refers to polypeptides that include naturally occurring truncated GLP-1 polypeptides (GLP-1(7-37)OH and GLP-1(7-36)$NH_2$), GLP-1 fragments, GLP-1 analogs, and derivatives thereof. For purposes of the present invention, GLP-1 compounds also include Exendin-3 and Exendin-4, and analogs and derivatives thereof. GLP-1 compounds of the present invention have the ability to bind to the GLP-1 receptor and initiate a signal transduction pathway resulting in insulinotropic activity. Examples of GLP-1 compounds appropriate for use in the present invention are discussed more extensively below.

The term "insulinotropic activity" refers to the ability to stimulate insulin secretion in response to elevated glucose levels, thereby causing glucose uptake by cells and an associated decrease in plasma glucose levels. Insulinotropic activity can be assessed by methods known in the art, including using in vivo experiments and in vitro assays that measure GLP-1 receptor binding activity or receptor activation, e.g., assays employing pancreatic islet cells or insulinoma cells, as described in EP 619,322 to Gelfand, et al. (described in Example 1), and U.S. Pat. No. 5,120,712, respectively. Insulinotropic activity is routinely measured in humans by measuring insulin levels or C-peptide levels. A GLP-1 compound has insulinotropic activity if islet cells secrete insulin levels in the presence of the GLP-1 compound above background levels.

GLP-1 compounds can exist in at least two different forms. The first form is physiologically active and dissolves readily in aqueous solution at physiological pH (7.4). In contrast, the second form has little or no insulinotropic activity and is substantially insoluble in water at pH 7.4. Thus, the GLP-1 compound should be formulated under conditions that reduce the propensity of the GLP-1 compound to aggregate and generate an insoluble, inactive complex. The propensity of a particular GLP-1 compound under a given set of formulation conditions may be determined by measuring turbidity at 350 nm as described in Example 8.

Preferably the pre-mixed formulations encompassed by the present invention are comprised of a GLP-1 compound with insulinotropic activity that is equal to or greater than GLP-1 (7-37)OH. It is even more preferable that the GLP-1 compound have greater insulinotropic activity than GLP-1 (7-37)OH.

The term "basal insulin" used in the present invention refers to an insulin analog having basal activity or a formulation of an insulin or insulin analog that has basal activity. Generally, basal insulins are recognized in the art and exhibit protracted time action greater than 8 hours in standard models of diabetes. Preferably, the basal insulin has a basal activity of about 24 hours. Preferably, the basal insulin has a basal activity of 8 to 14 hours. Preferably, the basal insulin has a basal activity similar to that observed for commercial formulations of NPH, NPL, PZI, Ultralente, or insulin glargine.

The term "biphasic formulation" used in the present invention refers to a basal insulin that is substantially insoluble and a GLP-1 compound that is substantially soluble in the pre-mixed formulation. The basal insulin is substantially insoluble if after centrifugation of the mixture little or no insulin is detected in the supernatant. Preferably, the insoluble insulin in the formulation remains insoluble for an extended period of time under the conditions of storage. The protracted time action of these basal insulins is due in part to the slow rate of absorption and dissociation of a hexamer of insulin to the active insulin monomers after injection.

The term "solution formulation" used in the present invention refers to a basal insulin that is substantially soluble and a GLP-1 compound that is substantially soluble in the pre-mixed formulation. Examples of soluble basal insulins include insulins wherein the isoelectric point (pI) is shifted and acylated insulins. Insulin glargine (Lantus®) is one example of a pI shifted insulin. By addition to and or substitution of basic amino acids in regular human insulin, the pI is shifted from about 5.5 to a more neutral pH. For example, addition of two arginines at the C-terminal end of the B chain results in a shift of the pI to about 7. This pI shifted insulin analog would be soluble at an acidic or basic pH. Alternatively, the pI can be shifted more acidic by addition to and or substitution of acidic amino acids in regular human insulin. This pI shifted insulin analog would be soluble at a basic pH. Then, upon injection of either solution, the pH will adjust to a physiological pH sufficiently close to the pI of the insulin analog, the net charge will be zero, and the result will be precipitation of the insulin. The precipitated insulin then slowly dissolves and is absorbed into the blood over a period of time to achieve the desired basal activity.

Acylated insulins are generally described as an insulin or insulin analog having lipophilic substituents on the insulin. The lipophilic substituents interact with proteins in the blood such as albumin. The result is that the insulin is preserved for a longer period of time while circulating in the blood. In addition, the lipophilic substituents may provide increased stability by protecting the insulin from degradative enzymes. Further, the lipophilic substituents may delay absorption of the insulin into the blood from the injection site.

The ratio of GLP-1 compound to basal insulin is such that after administration of the formulation, the plasma levels are maintained within the efficacious range. Preferably, serum levels of a GLP-1 compound that has insulinotropic activity within 2-fold that of GLP-1(7-37)OH is maintained between about 30 picomoles/liter and about 200 picomoles/liter. Optimum serum levels will be higher for GLP-1 compounds that are less active than GLP-1(7-37)OH or lower for GLP-1 compounds that are more active than GLP-1(7-37)OH. In general, the mixture will be formulated such that about 0.1 to about 5 mg of GLP-1 compound will be administered per day. Preferably, the GLP-1 compound will be administered in the range of 0.1 to 2 mg/day. More preferably, the GLP-1 compound will be administered in the range of 0.5 to 2 mg/day. The concentration of the GLP-1 compound may be adjusted upwards or downwards depending on the activity of the GLP-1 compound selected. The concentration of the GLP-1 compound in the premixed formulation in general is in the range of 0.1 to 20 mg/ml. Preferably, concentration of the GLP-1 compound in the premixed formulation is in the range of 0.1 to 10 mg/ml. More preferably, the concentration of the GLP-1 compound is in the range of 0.1 to 5 mg/ml.

In general, the mixture will be formulated such that about 0.01 to about 1 U/kg of basal insulin will be administered per day. Preferably, the basal insulin will be administered in the range of 0.05 to 0.5 U/kg/day. More preferably, the basal insulin will be administered in the range of 0.05 to 0.3 U/kg/day.

The various pre-mixed formulations comprising a GLP-1 compound and a basal insulin of the present invention may optionally encompass a pharmaceutically acceptable buffer. However, the selection, concentration, and pH of the buffer shall be such that the GLP-1 compound remains substantially soluble in the formulation and retains insulinotropic activity and the basal insulin retains a protracted action profile. Examples of pharmaceutically acceptable buffers include phosphate buffers like dibasic sodium phosphate, TRIS, acetate, such as sodium acetate, citrate, such as sodium citrate, sodium tartarate, basic amino acids such as histidine, lysine or arginine, or neutral amino acids such as glycine and glycyl-glycine. Other pharmaceutically acceptable buffers are known in the art. Preferably, the buffer is selected from the group consisting of acetate, phosphate and TRIS. The skilled artisan will recognize that the selection of the buffer is dependent upon the desired pH and the pKa of the buffer. Thus, in the case where the desired pH is in the physiological range, the buffers with a pKa in that range are desired. Preferably the buffer is phosphate and TRIS when the pH is in the physiological range. Where the desired pH is in the basic range, a preferred buffer is TRIS and where the desired pH is in the acidic range, a preferred buffer is acetate. Preferably, the concentration of a buffer is between about 1 mM and 30 mM. Even more preferably, the concentration is between about 4 mM and 14 mM The pH of the pre-mixed formulation is adjusted to provide acceptable stability, to maintain the solubility and insulinotropic activity of the GLP-1 compound and the protracted action profile of the basal insulin and be acceptable for parenteral administration. When the basal insulin is insoluble, the pH of the pre-mixed formulation is preferably adjusted to between about 7.0 and about 8.5, more preferably the pH is between about 7.4 and 8.0, even more preferably the pH is between about 7.4 and 7.8. Most preferably, the pH is between about 7.6 and 7.8, most preferably 7.8.

However, when the basal insulin is a pI shifted insulin analog, the pH is adjusted to maintain solubility of both the GLP-1 compound and the basal insulin analog in an aqueous medium. For example, human insulin has a pI of about 5.5. When the pI is shifted up to about 7 as a result of the addition of basic amino acids, the pH is adjusted to slightly acidic or slightly basic pH to maintain solubility. The pH can be adjusted to less than about 6, less than about 5, less than about 4. The pH can also be adjusted to greater than about 8, greater than about 9, greater than about 10. When the pI shifted insulin analog is insulin glargine, the pH is adjusted to about 4. Alternatively, when the pI shifted insulin analog is insulin glargine, the pH can be adjusted to about 8.

The pH is also dependent upon the GLP-1 compounds used in the premixed formulations. In general, the pH of the GLP-1 compounds is between about 4 and about 10. The pH is adjusted to slightly acidic or slightly basic pH to maintain solubility dependent on the pI of the GLP-1 compound. When the pI of the GLP-1 compound is about 7 then the pH can be adjusted to less than about 6, less than about 5, about 4. The pH can also be adjusted to greater than about 8, greater than about 9, about 10. For example, GLP-1 compounds with glutamic acid at position 22 can be formulated at an acidic pH and still remain soluble. Preferably, the pH of GLP-1 compounds with glutamic acid at position 22 is between about 4 and 6. More preferably the pH is about 4. Other GLP-1 compounds with a neutral amino acid at position 22 can be formulated at physiological or higher pH and still remain soluble. Preferably, the pH of GLP-1 compounds with a neutral amino acid at position 22 is between about 7 and 10. More preferably the pH is between about 7 and 8.5. Exendin-3 and Exendin-4 can be formulated at an acidic pH and still remain soluble. Preferably, the pH of Exendin-3 or Exendin-4 is between about 4 and 6. More preferably the pH is about 4.

The pre-mixed formulations of the present invention may optionally encompass a preservative. However, the selection and concentration of the preservative shall be such that the GLP-1 compound remains substantially soluble in the formulation and retains insulinotropic activity and the basal insulin retains a protracted action profile. Preservative refers to a compound that is added to a pharmaceutical formulation to act as an anti-microbial agent. A parenteral formulation must meet guidelines for preservative effectiveness to be a commercially viable multi-use product. Among preservatives known in the art as being effective and acceptable in parenteral formulations are phenolic preservatives, alkylparabens, benzyl alcohol, chlorobutanol, resorcinol, and other similar preservatives, and various mixtures thereof. Examples of phenolic derivatives include cresols and phenol or a mixture of cresols and phenol. Examples of cresols include meta-cresol, ortho-cresol, para-cresol, chloro-cresol, or mixtures thereof. Alkylparaben refers to a $C_1$ to $C_4$ alkyl paraben, or mixtures thereof. Examples of alkylparabens include methylparaben, ethylparaben, propylparaben, or butylparaben. The concentration of the preservative is known to one skilled in the art. The concentrations must be sufficient to maintain preservative effectiveness by retarding microbial growth. Preferably, the preservative is a phenol derivative. More preferably the preservative is cresol, phenol, or a mixture of cresol and phenol. Even more preferably the preservative is meta-cresol, phenol, or a mixture of meta-cresol and phenol.

For biphasic formulations, the preferred preservative is a mixture of meta-cresol and phenol. In general, the concentration of meta-cresol is between about 0.1 to about 4.0 mg/mL. The preferred concentration of meta-cresol is about 1.6 mg/mL. In general, the concentration of phenol is between about 0.1 to about 2.0 mg/mL. The preferred concentration of phenol is about 0.65 mg/mL.

For soluble formulations, the preferred preservative is meta-cresol or phenol. In general, the concentration of meta-cresol is between about 2.0 to about 8.0 mg/mL, about 2.5 mg/mL to about 4.5 mg/mL, and about 2.0 mg/mL to about 4.0 mg/mL. A most preferred concentration of preservative in the final mixture is about 2.7 mg/mL. In another embodiment, the concentration of phenol is between about 2.0 to about 10.0 mg/mL, and about 4.0 to about 8.0 mg/mL. A most preferred concentration of preservative in the final mixture is about 5.0 mg/mL.

In general, insulins are converted to a hexamer complex by dissolving the insulin in a diluent containing the preservative in suitable quantities at a pH of about 7 to about 8 and then adding zinc. However, the selection and amount of preservative and zinc shall be such that the GLP-1 compound remains substantially soluble in the formulation and retains insulinotropic activity and the basal insulin retains a protracted action profile. Zinc is preferably added as a zinc salt, such as, without limitation, zinc acetate, zinc bromide, zinc chloride, zinc fluoride, zinc iodide, and zinc sulfate. The skilled artisan will recognize that there are may other zinc salts which also might be used to make the insulin analog complexes that are part of the present invention. Preferably, the zinc salts are zinc acetate, zinc oxide, or zinc chloride.

In general, the hexamer complex consists of two zinc ions per hexamer of human insulin analog, and at least three molecules of a phenolic preservative selected from the group consisting of chlorocresol, m-cresol, phenol, and mixtures thereof.

The pre-mixed formulations of the present invention may optionally encompass an isotonicity agent. However, the selection and concentration of the isotonicity agent shall be such that the GLP-1 compound remains substantially soluble in the formulation and retains insulinotropic activity and the basal insulin retains a protracted action profile. Isotonicity agents refer to compounds that are tolerated physiologically and impart a suitable tonicity to the formulation to prevent the net flow of water across cell membranes. Examples of such compounds include glycerin (or glycerol), salts, e.g., NaCl, and sugars, e.g., dextrose, mannitol, and sucrose. These compounds are commonly used for such purposes at known concentrations. One or more isotonicity agents may be added to adjust the ionic strength or tonicity.

For biphasic formulations, a preferred isotonicity agent is glycerin. The concentration of glycerin is preferably between about 12 mg/mL and 25 mg/ml, preferably between about 12 mg/mL and 20 mg/ml, and more preferred is about 16 mg/ml.

For soluble formulations, the preferred isotonicity agent is NaCl. The concentration of NaCl is preferably between about 10 mM and 200 mM, more preferred is between about 50 mM and 150 mM, and most preferred is about 100 mM. In another 2.5 embodiment, the preferred isotonicity agent is mannitol. The concentration of the mannitol is preferably between about 1% (weight (w)/volume (v)) and 10% (w/v), and more preferred is between about 2% (w/v) and 8% (w/v). In another embodiment, the preferred isotonicity agent is glycerin. The concentration of the glycerin is preferably between about 12 mg/mL and 25 mg/ml, preferably between about 12 mg/mL and 20 mg/ml, and more preferred is about 17 mg/ml.

Soluble formulations of the present invention may optionally encompass a solubility enhancer. However, the selection and concentration of the solubility enhancer shall be such that the GLP-1 compound remains substantially soluble in the formulation and retains insulinotropic activity and the basal insulin remains substantially soluble in the formulation and retains a protracted action profile. Solubility enhancers provide stability to the basal insulin and the GLP-1 compound, such that the basal insulin and the GLP-1 compound remain soluble for an extended period of time under the conditions of storage. Preferably the solubility enhancer is nicotinamide. In general, the concentration of nicotinamide is between 0.01 and 2 molar. Other preferred ranges of nicotinamide concentration are: between 0.05 molar and 1.5 molar; between 0.1 molar and 1.0 molar; between 0.1 molar and 0.5 molar; between 0.5 molar and 1.0 molar; and between 0.15 molar and 0.25 molar.

Other additives, such as a pharmaceutically acceptable solubilizers like Tween 20® (polyoxyethylene (20) sorbitan monolaurate), Tween 40® (polyoxyethylene (20) sorbitan monopalmitate), Tween 80® (polyoxyethylene (20) sorbitan monooleate), Pluronic F68® (polyoxyethylene polyoxypropylene block copolymers), and PEG (polyethylene glycol) may optionally be added to the formulation. Although these additives are not necessarily required, they may be useful if the formulations will contact plastic materials.

Preferably, when injected, the premixed formulations of the present invention result in a glucose profile that is the same or better than that obtained when the GLP-1 compound and basal insulin are administered separately.

The pre-mixed formulations of the present invention are suitable to treat diseases or conditions wherein the physiological effects of administering GLP-1 or insulin improves the disease or condition.

Included are subjects with non-insulin dependent diabetes, insulin dependent diabetes, stroke (see WO 00/16797 by Efendic), myocardial infarction (see WO 98/08531 by Efendic), obesity (see WO 98/19698 by Efendic), catabolic changes after surgery (see U.S. Pat. No. 6,006,753 to Efendic), functional dyspepsia and irritable bowel syndrome (see WO 99/64060 by Efendic). Also included are subjects requiring prophylactic treatment with a GLP-1 compound, e.g., subjects at risk for developing non-insulin dependent diabetes (see WO 00/07617). Additional subjects include those with impaired glucose tolerance or impaired fasting glucose, subjects whose body weight is about 25% above normal body weight for the subject's height and body build, subjects with a partial pancreatectomy, subjects having one or more parents with non-insulin dependent diabetes, subjects who have had gestational diabetes and subjects who have had acute or chronic pancreatitis are at risk for developing non-insulin dependent diabetes.

The pre-mixed formulations of the present invention can be used to normalize blood glucose levels, prevent pancreatic β-cell deterioration, induce β-cell proliferation, stimulate insulin gene transcription, up-regulate IDX-1/PDX-1 or other growth factors, improve β-cell function, activate dormant β-cells, differentiate cells into β-cells, stimulate β-cell replication, inhibit β-cell apoptosis, regulate body weight, and induce weight loss.

The premixed formulations described herein can be used to treat subjects with a wide variety of diseases and conditions. The GLP-1 compounds encompassed in the premixed formulations of the present invention exert their biological effects by acting at a receptor referred to as the "GLP-1 receptor" (see Thorens, PNAS 89, 8641-8645 (1992)).

Subjects with diseases and/or conditions that respond favorably to GLP-1 receptor stimulation or to the administration of GLP-1 compounds can therefore be treated with the GLP-1 compounds of the present invention. These subjects are said to "be in need of treatment with GLP-1 compounds" or "in need of GLP-1 receptor stimulation."

The following provides an even more detailed discussion of the GLP-1 compounds and basal insulins useful in the premixed formulations of the present invention.

Representative examples of GLP-1 compounds that can be used in the pre-mixed formulations of the present invention include those known in the art such as the analogs disclosed in U.S. Pat. Nos. 5,118,666, 5,120,712, 5,512,549, 6,191,102, 5,977,071, 5,545,618, 5,705,483, 6,133,235, and in Adelhorst, et al., (1994) J. Biol. Chem. 269:6275.

The two naturally occurring truncated GLP-1 polypeptides are represented in formula I (SEQ ID NO: 1):

```
SEQ ID NO: 1
7    8    9    10   11   12   13   14   15   16   17

His-Ala-Glu-Gly-Thr-Phe-Thr-Ser-Asp-Val-Ser- 18   19   20   21   22   23   24   25   26   27   28

Ser-Tyr-Leu-Glu-Gly-Gln-Ala-Ala-Lys-Glu-Phe- 29   30   31   32   33   34   35   36   37

Ile-Ala-Trp-Leu-Val-Lys-Gly-Arg-Xaa
``` wherein:

Xaa at position 37 is Gly, or —$NH_2$.

The term "dipeptidyl peptidase IV (DPP IV) resistant" refers to GLP-1 molecules that have extended metabolic stability and improved biological activity because they are resistant to the endogenous enzyme, DPP IV. For example, DPP IV resistance can be determined using the method described in Example 2. A GLP-1 molecule is DPP IV resistant if in the presence of DPP IV the GLP-1 molecule has extended metabolic stability above that of native GLP-1. DPP IV resistant GLP-1 molecules can have an amino acid change at the DPP IV recognition site (position 8), or DPP IV resistant peptides can have an attached group that restricts the accessibility of DPP IV to the recognition site, or both.

A "GLP-1 fragment" is a polypeptide obtained after truncation of one or more amino acids from the N-terminus and/or C-terminus of GLP-1(7-37)OH or an analog or derivative thereof. The nomenclature used to describe GLP-1(7-37)OH is also applicable to GLP-1 fragments. For example, GLP-1(9-36)OH denotes a GLP-1 fragment obtained by truncating two amino acids from the N-terminus and one amino acid from the C-terminus. The amino acids in the fragment are denoted by the same number as the corresponding amino acid in GLP-1(7-37)OH. For example, the N-terminal glutamic acid in GLP-1(9-36)OH is at position 9; position 12 is occupied by phenylalanine; and position 22 is occupied by glycine, as in GLP-1(7-37)OH. For GLP-1(7-36)OH, the Glycine at position 37 of GLP-1(7-37) OH is deleted.

A "GLP-1 analog" has sufficient homology to GLP-1(7-37)OH or a fragment of GLP-1(7-37)OH such that the analog has insulinotropic activity. Preferably, a GLP-1 analog has the amino acid sequence of GLP-1(7-37)OH or a fragment thereof, modified so that from one, two, three, four or five amino acids differ from the amino acid in corresponding position of GLP-1(7-37)OH or a fragment of GLP-1(7-37)OH. In the nomenclature used herein to designate GLP-1 compounds, the substituting amino acid and its position is indicated prior to the parent structure. For example, $Glu^{22}$-GLP-1(7-37)OH designates a GLP-1 compound in which the glycine normally found at position 22 of GLP-1(7-37)OH has been replaced with glutamic acid; $Val^8$-$Glu^{22}$-GLP-1(7-37)OH designates a GLP-1 compound in which alanine normally found at position 8 and glycine normally found at position 22 of GLP-1(7-37)OH have been replaced with valine and glutamic acid, respectively.

Other GLP-1 compounds of the present invention include additions of one or more amino acids to the N-terminus and/or C-terminus of GLP-1. Preferably from one to six amino acids are added to the N-terminus and/or from one to eight amino acids are added to the C-terminus of GLP-1. It is preferred that GLP-1 analogs of this type have up to about thirty-nine amino acids. The amino acids in the extended GLP-1 analogs are denoted by the same number as the corresponding amino acid in GLP-1(7-37)OH. For example, the N-terminal amino acid of a GLP-1 analog obtained by adding two amino acids to the N-terminus of GLP-1(7-37) OH is at position 5; and the C-terminal amino acid of a GLP-1 compound obtained by adding one amino acid to the C-terminus of GLP-1(7-37)OH is at position 38. Amino acids 1-6 of an extended GLP-1 analog are preferably the same as or a conservative substitution of the amino acid at the corresponding position of GLP-1(1-37)OH. Amino acids 38-45 of an extended GLP-1 compound are preferably the same as or a conservative substitution of the amino acid at the corresponding position of Exendin-4.

A conservative substitution is the replacement of an amino acid with another amino acid that has the same net electronic charge and approximately the same size and shape. Amino acids with aliphatic or substituted aliphatic amino acid side chains have approximately the same size when the total number of carbon and heteroatoms in their side chains differs by no more than about four. They have approximately the same shape when the number of branches in the their side chains differs by no more than one. Amino acids with phenyl or substituted phenyl groups in their side chains are considered to have about the same size and shape. Preferably, a GLP-1 compound has the amino acid sequence of SEQ ID NO. 1 or is modified so that from one, two, three, four or five amino acids differ from SEQ ID NO: 1.

The amino acid sequence of Exendin-3 and Exendin-4 are represented in formula II (SEQ ID NO:2):

```
SEQ ID NO: 2
7    8    9    10   11   12   13   14   15   16   17

His-Xaa-Xaa-Gly-Thr-Phe-Thr-Ser-Asp-Leu-Ser- 18   19   20   21   22   23   24   25   26   27   28
```

```
                       -continued
    Lys-Gln-Met-Glu-Glu-Glu-Ala-Val-Arg-Leu-Phe- 29   30   31   32   33   34   35   36   37   38   39

Ile-Glu-Trp-Leu-Lys-Asn-Gly-Gly-Pro-Ser-Ser- 40   41   42   43   44   45

Gly-Ala-Pro-Pro-Pro-Ser
``` wherein:
Xaa at position 8 is Ser or Gly;
Xaa at position 9 is Asp or Glu; and
Ser at position 45 is Ser or Ser-NH$_2$.

Exendin-3 has Ser at position 8 and Asp at position 9. Exendin-4 has Gly at position 8 and Glu at position 9. Other GLP-1 compounds of the present invention include Exendin-3 and Exendin-4 agonists as described in WO99/07404, WO99/25727, WO99/25728, WO99/43708, WO00/66629, and US2001/0047084A1 and are herein incorporated by reference.

A preferred group of GLP-1 analogs are represented in formula III (SEQ ID NO:3):

```
SEQ ID NO: 3
7    8    9    10   11   12   13   14   15   16   17

Xaa-Xaa-Xaa-Gly-Xaa-Xaa-Thr-Xaa-Asp-Xaa-Xaa- 18   19   20   21   22   23   24   25   26   27   28

Xaa-Xaa-Xaa-Xaa-Xaa-Xaa-Xaa-Xaa-Xaa-Xaa-Phe- 29   30   31   32   33   34   35   36   37   38   39

Ile-Xaa-Xaa-Xaa-Xaa-Xaa-Xaa-Xaa-Xaa-Xaa-Xaa- 40   41   42   43   44   45

Xaa-Xaa-Xaa-Xaa-Xaa-Xaa
``` wherein:
Xaa at position 7 is: L-histidine, D-histidine, desamino-histidine, 2-amino-histidine, βhydroxy-histidine, homohistidine, α-fluoromethyl-histidine or α-methyl-histidine;
Xaa at position 8 is Ala, Gly, Ser, Thr, Leu, Ile, Val, Glu, Asp, or Lys;
Xaa at position 9 is Glu, Asp, Lys, Thr, Ser, Arg, Trp, Phe, Tyr, or His;
Xaa at position 11 is Thr, Ala, Gly, Ser, Leu, Ile, Val, Glu, Asp, Arg, His, or Lys;
Xaa at position 12 is His, Trp, Phe, or Tyr
Xaa at position 14 is Ser, Ala, Gly, Thr, Leu, Ile, Val, Glu, Asp, or Lys;
Xaa at position 16 is Val, Ala, Gly, Ser, Thr, Leu, Ile, Tyr, Glu, Asp, Trp, His, Phe, or Lys;
Xaa at position 17 is Ser, Ala, Gly, Thr, Leu, Ile, Val, Glu, Asp, or Lys;
Xaa at position 18 is Ser, Ala, Gly, Thr, Leu, Ile, Val, Glu, Asp, His, Pro, Arg, or Lys;
Xaa at position 19 is Tyr, Phe, Trp, Glu, Asp, Gly, Gln, Asn, Arg, Cys, or Lys;
Xaa at position 20 is Leu, Ala, Gly, Ser, Thr, Ile, Val, Glu, Asp, Met, or Lys;
Xaa at position 21 is Glu, Asp, or Lys;
Xaa at position 22 is Gly, Ala, Ser, Thr, Leu, Ile, Val, Glu, Asp, or Lys;
Xaa at position 23 is Gln, Asn, Arg, Glu, Asp, His, or Lys;
Xaa at position 24 is Ala, Gly, Ser, Thr, Leu, Ile, Val, Arg, Glu, Asp, or Lys;
Xaa at position 25 is Ala, Gly, Ser, Thr, Leu, Ile, Val, Glu, Asp, or Lys;
Xaa at position 26 is Lys, Arg, Gln, Glu, Asp, Trp, Tyr, Phe, or His;
Xaa at position 27 is Glu, Asp, Ala, His, Phe, Tyr, Trp, Arg, Leu, or Lys;
Xaa at position 30 is Ala, Gly, Ser, Thr, Leu, Ile, Val, Glu, Asp, His, or Lys;
Xaa at position 31 is Trp, Phe, Tyr, Glu, Asp, Ser, Thr, Arg, or Lys;
Xaa at position 32 is Leu, Gly, Ala, Ser, Thr, Ile, Val, Glu, Asp, or Lys;
Xaa at position 33 is Val, Gly, Ala, Ser, Thr, Leu, Ile, Glu, Asp, Arg, or Lys;
Xaa at position 34 is Lys, Arg, Glu, Asp, Asn, or His;
Xaa at position 35 is Gly, Ala, Ser, Thr, Leu, Ile, Val, Glu, Asp, Arg, Trp, Tyr, Phe, Pro, His, or Lys;
Xaa at position 36 is Arg, Lys, Glu, Asp, Thr, Ser, Trp, Tyr, Phe, Gly, or His;
Xaa at position 37 is Gly, Ala, Ser, Thr, Leu, Ile, Val, Glu, Asp, His, Lys, Arg, Trp, Tyr, Phe, Pro, Pro-NH$_2$ or is deleted;
Xaa at position 38 is Arg, Lys, Glu, Asp, Ser, or His, or is deleted;
Xaa at position 39 is Arg, Lys, Glu, Asp, Ser, or His, or is deleted;
Xaa at position 40 is Asp, Glu, Gly, or Lys, or is deleted;
Xaa at position 41 is Phe, Trp, Tyr, Glu, Asp, Ala, or Lys, or is deleted;
Xaa at position 42 is Ser, Pro, Lys, Glu, or Asp, or is deleted;
Xaa at position 43 is Ser, Glu, Asp, Pro, or Lys, or is deleted;
Xaa at position 44 is Gly, Glu, Asp, Pro, or Lys, or is deleted; and
Xaa at position 45 is Ala, Val, Glu, Asp, Ser, or Lys, or Ala-NH$_2$, Val-NH$_2$, Glu-NH$_2$, Asp-NH$_2$, Ser-NH$_2$, or Lys-NH$_2$, or is deleted, or a C-1-6-ester, or amide, or C-1-6-alkylamide, or C-1-6-dialkylamide thereof; provided that when the amino acid at position 37, 38, 39, 40, 41, 42, 43, or 44 is deleted, then each amino acid downstream of that amino acid is also deleted.

A preferred group of GLP-1 analogs are:

```
HVEGTFTSDVSSYLEEQAAKEFIAWLVKGRG    or  G-NH2

HVEGTFTSDVSSYLEEQAAKEFIAWLIDGGPSSGRPPPS  or  S-NH2

HVEGTFTSDVSSYLEEQAAKEFIAWLVKGRGSSGDPPPS  or  S-NH2

HVEGTFTSDVSSYLEEQAAKEFIAWLVKGRPSSGDPPPS  or  S-NH2

HVEGTFTSDVSSYLEEQAAKEFIAWLIKGGPSSGDPPPS  or  S-NH2

HVEGTFTSDVSSYLEEQAAKEFIAWLIKGGPSSGDPPPS  or  S-NH2

HVEGTFTSDVSSYLEEQAAKEFIAWLIKGGPSSGDPPPS  or  S-NH2

HVEGTFTSDVSSYLEEQAAXEFIAWLVKGRPSSGAPPPS  or  S-NH2

HVEGTFTSDVSSYLEEQAAKEFIAWLVKGRPSSGDPPPS  or  S-NH2

HVEGTFTSDVSSYLEEQAAKEFIAWLIKGGPSSGAPPPS  or  S-NH2

HVEGTFTSDVSSYLEEQAVKEFIAWLIKGGPSSGAPPPS  or  S-NH2
```

HVEGTFTSDVSSYLEEQAVKEFIAWLVKGGPSSGAPPPS or S-NH2

HVEGTFTSDVSSYLEEQAVKEFIAWLIKGGPSSGDPPPS or S-NH2

NVEGTFTSDVSSYLEEQAAKEFIAWLIKGGGSSGDPPPS or S-NH2

RVEGTFTSDVSSYLEEQAAKEFIAWLIKGPGSSGDPPPS or S-NH2

HVEGTFTSDVSSYLEEQAAKEFIAWLIKGGSPSGDPPPS or S-NH2

HVEGTFTSDVSSYLEEQAAKEFIAWLIKGGPSSGDPPS or S-NH2

HVEGTFTSDVSSYLEEQAAKEFIAWLIKGGPSSGDPPPS or S-NH2

HVEGTFTSDVSSYLEEQAAKEFIAWLIKGGPSSGDAPPS or S-NH2

HVEGTFTSDVSSYLEEQAAKEFIAWLIKGGPSSGDPAPS or S-NH2

HVEGTFTSDVSSYLEEQAAKEFIAWLIKGGPSSGDPPAS or S-NH2

HVEGTFTSDVSSYLEEQAAKEFIAWLIKGGPSSGDAAAS or S-NH2

EVEGTFTSDWSSYLEGQAAKEFIAWLIKGGPSSGAPPPS or S-NH2

HVEGTFTSDWSSYLEGQAAKEFIAWLIKGGPSSGAPPPH or H-NH2

HVEGTFTSDVSSYLEGQAAKEFIAWLIKGGPSSGAPPPS or S-NH2

HVEGTFTSDVSSYLEGQAAKEFIAWLIKGGPSSGDPPPS or S-NH2

HVEGTFTSDWSSYLEGQAAKEFIAWLIKGGPSSGAPPPSH or H-NH2

HVEGTFTSDWSSYLEGQAAKEFIAWLIKGGPHSSGAPPPS or S-NH2

HVEGTFTSDVSSYLEGQAAKEFIAWLVKGRGSSGAPPPS or S-NH2

HVEGTFTSDVSSYLEGQAAKEFIAWLVKGGPSSGAPPPS or S-NH2

HVEGTFTSDVSSYLEEQAAKEFIAWLVKGGPSSGAPPPS or S-NH2

HVEGTFTSDVSSYLEEQAAKEFIAWLVKGRGSSGAPPPS or S-NH2

HVEGTFTSDVSSYLEEQAVKEFIAWLIKGRGSSGAPPPS or S-NH2

HVEGTFTSDWSSYLEEQAAKEFIAWLIKGRGSSGAPPPS or S-NH2

HVEGTFTSDVSSYLEEQAAKEFIAWLIKGRGHSSGAPPPS or S-NH2

HVEGTFTSDVSSYLEEQAAKEFIAWLVKGRGHSSGAPPPS or S-NH2

HVEGTFTSDWSSYLEEQAAKEFIAWLIKGGPHSSGAPPPSH or H-NH2

HVEGTFTSDWSSYLEEQAAKEFIAWLIKGGPSSGAPPPSH or H-NH2

HVEGTFTSDVSWYLEGQAVKEFIAWLIKGGPHSSGAPPPS or S-NH2

HVEGTFTSDVSSYLEEQAVKEFIAWLIKGGPSSGAPPPS or S-NH2

HVEGTFTSDVSSYLEEQAVKEFIAWLIKGGPSSGAPPPSH or H-NH2

HVEGTFTSDWSSYLEEQAVKEFIAWLIKGGPSSGAPPPS or S-NH2

HVEGTFTSDWSSYLEEQAVKEFIAWLIKGGPSSGAPPPSH or H-NH2

HVEGTFTSDWSSYLEEQAVKEFIAWLIKGGPHSSGAPPPS or S-NH2

HVEGTFTSDWSKYLEEQAVKEFIAWLIKGGPSSGAPPPSH or H-NH2

HVEGTFTSDVSSYLEEQAVKEFIAWLIKGGPSSGAPPPRG or G-NH2

HVEGTFTSDVSSYLEEQAVKEFIAWLIKGGPSSGAPPPRG or G-NH$_2$

HVEGTFTSDVSSYLEEQAAKEFIAWLVKGGPSSGAPPPS or S-NH$_2$

HVEGTFTSDVSSYLEEQAAKEFIAWLVDGGPSSGRPPPS or S-NH$_2$

HVEGTFTSDVSSYLEEQAAKEFIAWLVDGGPSSGRPPPS or S-NH$_2$

HVEGTFTSDVSSYLEEQAAKEFIAWLVDGGPSSGKPPPS or S-NH2

HVEGTFTSDVSSYLEEQAAKEFIAWLVDGGPSSGRG or G-NH2

HVEGTFTSDVSSYLEEQAAKEFIAWLIKGGPSSGAPPPS or S-NH2

HVEGTFTSDVSSYLEEQAAKEFIAWLVKGGPSWGAPPPS or S-NH2

HVEGTFTSDVSSYLEEQAAKEFIAWLIKGGPSSGAPPPGPS or S-NH2

HVEGTFTSDVSSYLEEQAAKEFIAWLIKGGPSSGAPPPGPSGPS or S-NH2

HVEGTFTSDVSSYLEEQAVKEFIAWLVKGGPSSGAPPPS or S-NH2

Another preferred group of GLP-1 analogs is represented in formula IV (SEQ ID NO:4):

```
 7   8   9  10  11  12  13  14  15  16  17
His-Xaa-Glu-Gly-Thr-Phe-Thr-Ser-Asp-Val-Ser- 18  19  20  21  22  23  24  25  26  27  28
Ser-Tyr-Leu-Glu-Xaa-Xaa-Ala-Ala-Lys-Xaa-Phe- 29  30  31  32  33  34  35  36  37
Ile-Xaa-Trp-Leu-Val-Lys-Gly-Arg-R
``` wherein:
Xaa at position 8 is Gly, Ala, Val, Leu, Ile, Ser, or Thr;
Xaa at position 22 is Asp, Glu, Gln, Asn, Lys, Arg, Cys, or Cysteic Acid;
Xaa at position 23 is His, Asp, Lys, Glu, or Gln;
Xaa at position 27 is Ala, Glu, His, Phe, Tyr, Trp, Arg, or Lys;
Xaa at position 30 is Glu, Asp, Ser, or His;
R is: Lys, Arg, Thr, Ser, Glu, Asp, Trp, Tyr, Phe, His, —NH$_2$.

It is also preferable that the GLP-1 compounds of the present invention have other combinations of substituted amino acids. The present invention encompasses a GLP-1 compound comprising the amino acid sequence of formula V (SEQ ID NO:5)

```
Xaa7-Xaa8-Glu-Gly-Thr-Xaa12-Thr-Ser-Asp-Xaa16-
Ser-Xaa18-Xaa19-Xaa20-Glu-Xaa22-Gln-Ala-Xaa25-Lys-
Xaa27-Phe-Ile-Xaa30-Trp-Leu-Xaa33-Lys-Gly-Arg-
Xaa37
Formula V (SEQ ID NO: 5)
``` wherein:
Xaa$_7$ is: L-histidine, D-histidine, desamino-histidine, 2-amino-histidine, β-hydroxy-histidine, homohistidine, α-fluoromethyl-histidine, or α-methyl-histidine;
Xaa$_8$ is: Ala, Gly, Val, Leu, Ile, Ser, or Thr;
Xaa$_{12}$ is: Phe, Trp, or Tyr;
Xaa$_{16}$ is: Val, Trp, Ile, Leu, Phe, or Tyr;
Xaa$_{18}$ is: Ser, Trp, Tyr, Phe, Lys, Ile, Leu, Val;
Xaa$_{19}$ is: Tyr, Trp, or Phe;
Xaa$_{20}$ is: Leu, Phe, Tyr, or Trp;
Xaa$_{22}$ is: Gly, Glu, Asp, Lys;
Xaa$_{25}$ is: Ala, Val, Ile, or Leu;
Xaa$_{27}$ is: Glu, Ile, or Ala;
Xaa$_{30}$ is: Ala or Glu Xaa₃₃ is: Val, or Ile; and Xaa₃₇ is: Gly, His, NH₂, or is absent.

The present invention also encompasses a GLP-1 compound comprising the amino acid sequence of formula VI (SEQ ID NO:6)

Xaa₇-Xaa₈-Glu-Gly-Thr-Phe-Thr-Ser-Asp-Xaa₁₆-Ser-Xaa₁₈-Tyr-Leu-Glu-Xaa₂₂-Gln-Ala-Xaa₂₅-Lys-Glu-Phe-Ile-Ala-Trp-Leu-Xaa₃₃-Lys-Gly-Arg-Xaa₃₇
Formula VI (SEQ ID NO: 6)

wherein:
Xaa₇ is: L-histidine, D-histidine, desamino-histidine, 2-amino-histidine, β-hydroxy-histidine, homohistidine, α-fluoromethyl-histidine, or α-methyl-histidine;
Xaa₈ is: Gly, Ala, Val, Leu, Ile, Ser, or Thr;
Xaa₁₆ is: Val, Phe, Tyr, or Trp;
Xaa₁₈ is: Ser, Tyr, Trp, Phe, Lys, Ile, Leu, or Val;
Xaa₂₂ is: Gly, Glu, Asp, or Lys;
Xaa₂₅ is: Ala, Val, Ile, or Leu;
Xaa₃₃ is: Val or Ile; and
Xaa₃₇ is: Gly, NH₂, or is absent.

It is preferred that the backbone of the GLP-1 analogs of formula I, II, III, IV, V, and VI comprise an amino acid other than alanine at position 8 (position 8 analogs). Preferred amino acids at position 8 are glycine, valine, leucine, isoleucine, serine, threonine, or methionine and more preferably are valine or glycine. The backbone may also include L-histidine, D-histidine, or modified forms of histidine such as desamino-histidine, 2-amino-histidine, β-hydroxy-histidine, homohistidine, α-fluoromethyl-histidine, or α-methyl-histidine at position 7. It is preferable that these position 8 analogs contain one or more additional changes at positions 12, 16, 18, 19, 20, 22, 25, 27, 30, 33, and 37 compared to the corresponding amino acid of native GLP-1(7-37)OH. It is more preferable that these position 8 analogs contain one or more additional changes at positions 16, 18, 22, 25 and 33 compared to the corresponding amino acid of native GLP-1(7-37)OH.

Even more preferred are GLP-1 analogs of formula I, II, III, IV, V, and VI wherein not more than 6 amino acids differ from the corresponding amino acid in native GLP-1(7-37)OH, GLP-1(7-36)NH₂, or Exendin-4. Most preferred are GLP-1 analogs of formula I, II, III, and IV wherein between 1 and 5 amino acids differ from the corresponding amino acid in native GLP-1(7-37)OH, GLP-1(7-36)NH₂, or Exendin-4.

Other preferred GLP-1 analogs have the sequence of GLP-1(7-37)OH except that the amino acid at position 8 is preferably glycine, valine, leucine, isoleucine, serine, threonine, or methionine and more preferably valine or glycine and position 22 is glutamic acid, lysine, aspartic acid, or arginine and more preferably glutamic acid or lysine.

Other preferred GLP-1 analogs have the sequence of GLP-1(7-37)OH except that the amino acid at position 8 is preferably glycine, valine, leucine, isoleucine, serine, threonine, or methionine and more preferably valine or glycine and position 30 is glutamic acid, aspartic acid, serine, or histidine and more preferably glutamic acid.

Other preferred GLP-1 analogs have the sequence of GLP-1(7-37)OH except that the amino acid at position 8 is preferably glycine, valine, leucine, isoleucine, serine, threonine, or methionine and more preferably valine or glycine and position 37 is histidine, lysine, arginine, threonine, serine, glutamic acid, aspartic acid, tryptophan, tyrosine, phenylalanine and more preferably histidine.

In a preferred embodiment, the GLP-1 analog is GLP-1(7-37)OH wherein the amino acid at position 12 is selected from the group consisting of tryptophan or tyrosine. It is more preferred that in addition to the substitution at position 12, the amino acid at position 8 is substituted with glycine, valine, leucine, isoleucine, serine, threonine, or methionine and more preferably valine or glycine. It is even more preferred that in addition to the substitutions at position 12 and 8, the amino acid at position 22 is substituted with glutamic acid.

In another preferred embodiment, the GLP-1 analog is GLP-1(7-37)OH wherein the amino acid at position 16 is selected from the group consisting of tryptophan, isoleucine, leucine, phenylalanine, or tyrosine. It is more preferred that in addition to the substitution at position 16, the amino acid at position 8 is substituted with glycine, valine, leucine, isoleucine, serine, threonine, or methionine and more preferably valine or glycine. It is even more preferred that in addition to the substitutions at position 16 and 8, the amino acid at position 22 is substituted with glutamic acid. It is also preferred that in addition to the substitutions at positions 16 and 8, the amino acid at position 30 is substituted with glutamic acid. It is also preferred that in addition to the substitutions at positions 16 and 8, the amino acid at position 37 is substituted with histidine.

In another preferred embodiment, the GLP-1 analog is GLP-1(7-37)OH wherein the amino acid at position 18 is selected from the group consisting of tryptophan, tyrosine, phenylalanine, lysine, leucine, or isoleucine, preferably tryptophan, tyrosine, and isoleucine. It is more preferred that in addition to the substitution at position 18, the amino acid at position 8 is substituted with glycine, valine, leucine, isoleucine, serine, threonine, or methionine and more preferably valine or glycine. It is even more preferred that in addition to the substitutions at position 18 and 8, the amino acid at position 22 is substituted with glutamic acid. It is also preferred that in addition to the substitutions at positions 18 and 8, the amino acid at position 30 is substituted with glutamic acid. It is also preferred that in addition to the substitutions at positions 18 and 8, the amino acid at position 37 is substituted with histidine.

In another preferred embodiment, the GLP-1 analog is GLP-1(7-37)OH wherein the amino acid at position 19 is selected from the group consisting of tryptophan or phenylalanine, preferably tryptophan. It is more preferred that in addition to the substitution at position 19, the amino acid at position 8 is substituted with glycine, valine, leucine, isoleucine, serine, threonine, or methionine and more preferably valine or glycine. It is even more preferred that in addition to the substitutions at position 19 and 8, the amino acid at position 22 is substituted with glutamic acid. It is also preferred that in addition to the substitutions at positions 19 and 8, the amino acid at position 30 is substituted with glutamic acid. It is also preferred that in addition to the substitutions at positions 19 and 8, the amino acid at position 37 is substituted with histidine.

In another preferred embodiment, the GLP-1 analog is GLP-1(7-37)OH wherein the amino acid at position 20 is phenylalanine, tyrosine, or tryptophan. It is more preferred that in addition to the substitution at position 20, the amino acid at position 8 is substituted with glycine, valine, leucine, isoleucine, serine, threonine, or methionine and more preferably valine or glycine. It is even more preferred that in addition to the substitutions at position 20 and 8, the amino acid at position 22 is substituted with glutamic acid. It is also preferred that in addition to the substitutions at positions 20 and 8, the amino acid at position 30 is substituted with glutamic acid. It is also preferred that in addition to the substitutions at positions 20 and 8, the amino acid at position 37 is substituted with histidine.

In another preferred embodiment, the GLP-1 analog is GLP-1(7-37)OH wherein the amino acid at position 25 is selected from the group consisting of valine, isoleucine, and leucine, preferably valine. It is more preferred that in addition to the substitution at position 25, the amino acid at position 8 is substituted with glycine, valine, leucine, isoleucine, serine, threonine, or methionine and more preferably valine or glycine. It is even more preferred that in addition to the substitutions at position 25 and 8, the amino acid at position 22 is substituted with glutamic acid. It is also preferred that in addition to the substitutions at positions 25 and 8, the amino acid at position 30 is substituted with glutamic acid. It is also preferred that in addition to the substitutions at positions 25 and 8, the amino acid at position 37 is substituted with histidine.

In another preferred embodiment, the GLP-1 analog is GLP-1(7-37)OH wherein the amino acid at position 27 is selected from the group consisting of isoleucine or alanine. It is more preferred that in addition to the substitution at position 27, the amino acid at position 8 is substituted with glycine, valine, leucine, isoleucine, serine, threonine, or methionine and more preferably valine or glycine. It is even more preferred that in addition to the substitutions at position 27 and 8, the amino acid at position 22 is substituted with glutamic acid. It is also preferred that in addition to the substitutions at positions 27 and 8, the amino acid at position 30 is substituted with glutamic acid. It is also preferred that in addition to the substitutions at positions 27 and 8, the amino acid at position 37 is substituted with histidine.

In another preferred embodiment, the GLP-1 analog is GLP-1(7-37)OH wherein the amino acid at position 33 is isoleucine. It is more preferred that in addition to the substitution at position 33, the amino acid at position 8 is substituted with glycine, valine, leucine, isoleucine, serine, threonine, or methionine and more preferably valine or glycine. It is even more preferred that in addition to the substitutions at position 33 and 8, the amino acid at position 22 is substituted with glutamic acid. It is also preferred that in addition to the substitutions at positions 33 and 8, the amino acid at position 30 is substituted with glutamic acid. It is also preferred that in addition to the substitutions at positions 33 and 8, the amino acid at position 37 is substituted with histidine.

It is preferable that the GLP-1 compounds of formula I, II, III, V, V, or VI have 6 or fewer changes compared to the corresponding amino acids in native GLP-1(7-37)OH.

More preferred analogs have 5 or fewer changes compared to the corresponding amino acids in native GLP-1(7-37)OH or have 4 or fewer changes compared to the corresponding amino acids in native GLP-1(7-37)OH or have 3 changes compared to the corresponding amino acids in native GLP-1(7-37)OH.

Some preferred GLP-1 compounds of formula I, II, III, IV, V, and VI having multiple substitutions include GLP-1(7-37)OH wherein position 8 is valine or glycine, position 22 is glutamic acid, position 16 is tyrosine, leucine or tryptophan, position 18 is tyrosine, tryptophan, or isoleucine, position 25 is valine and position 33 is isoleucine. Other preferred GLP-1 compounds include the following: Val$^8$-Tyr$^{16}$-GLP-1(7-37)OH, Val$^8$-Tyr$^{12}$-Glu$^{22}$-GLP-1(7-37)OH, Val$^8$-Tyr$^{16}$-Phe$^{19}$-GLP-1(7-37)OH, Val$^8$-Tyr$^{16}$-Glu$^{22}$-GLP-1(7-37)OH, Val$^8$-Trp$^{16}$-Glu$^{22}$-GLP-1(7-37)OH, Val$^8$-Leu$^{16}$-Glu$^{22}$-GLP-1(7-37)OH, Val$^8$-Ile$^{16}$-Glu$^{22}$-GLP-1(7-37)OH, Val$^8$-Phe$^{16}$-Glu$^{22}$-GLP-1(7-37)OH, Val$^8$-Trp$^{18}$-Glu$^{22}$-GLP-1(7-37)OH, Val$^8$-Tyr$^{18}$-Glu$^{22}$-GLP-1(7-37)OH, Val$^8$-Phe$^{18}$-Glu$^{22}$-GLP-1(7-37)OH, and Val$^8$-Ile$^{18}$-Glu$^{22}$-GLP-1(7-37)OH.

Substitutions at the positions disclosed herein result in a GLP-1 compound with increased potency compared to the potency of Val$^8$-GLP-1(7-37)OH. The GLP-1 compounds of the present invention generally are between 3 and 6-fold more potent than Val$^8$-GLP-1(7-37)OH. For example, table 8 and 9 provide a list of GLP-1 compounds with an in vitro potency compared to that obtained for GLP-1(7-37)OH and Val$^8$-GLP-1(7-37)OH, respectively. Preferably, the analogs are greater than 3-fold more potent than GLP-1(7-37)OH or Val$^8$-GLP-1(7-37)OH. The in vitro potencies disclosed in table 8 and 9 are generally representative of in vivo potency relative to GLP-1(7-37)OH or Val$^8$-GLP-1(7-37)OH.

Furthermore, many of these more potent analogs have a reduced propensity to aggregate and thus, have increased stability. GLP-1 compounds can exist in at least two different forms. The first form is physiologically active and dissolves readily in aqueous solution at physiological pH (7.4). A second inactive form is readily produced when aqueous GLP-1 solutions are agitated, exposed to hydrophobic surfaces or have large air/water interfaces. The tendency to convert to the insoluble form considerably complicates the production of commercial quantities of active GLP-1 compounds. Thus, GLP-1 compounds that have a reduced propensity to aggregate in solution and are more potent than GLP-1(7-37)OH or Val$^8$-GLP-1(7-37)OH are preferred. For example, the GLP-1 compounds Val$^8$-Glu$^{22}$-GLP-1(7-37)OH, Val$^8$-Glu$^{30}$-GLP-1(7-37)OH, and Val$^8$-His$^{37}$-GLP-1(7-37)OH show a markedly decreased propensity to aggregate in solution compared to GLP-1(7-37)OH or Val$^8$-GLP-1(7-37)OH (See tables 8 and 9). Thus, preferred GLP-1 compounds of the present invention have either a glutamic acid at position 22, a glutamic acid at position 30, or a histidine at position 37 or combinations thereof in addition to substitutions at other positions such as 12, 16, 18, 19, 20, 25, 27, and 33.

Preferred embodiments of formula I, II, III, IV, V, and VI include GLP-1 compounds that do not differ from GLP-1(7-34)OH or GLP-1(7-36)NH$_2$ by more than 6 amino acids, by more than 5 amino acids, by more than 4 amino acids, or by more than 3 amino acids. It is also preferable that the GLP-1 compounds of formula I, II, I, IV, V, and VI have valine or glycine at position 8 and glutamic acid at position 22. It is also preferable that the GLP-1 compounds of formula I and II have valine or glycine at position 8 and glutamic acid at position 30. It is also preferable that the GLP-1 compounds of formula I, II, III, IV, V, and VI have valine or glycine at position 8 and histidine at position 37.

Examples of GLP-1 analogs that have been shown to have a markedly decreased propensity to aggregate compared with GLP-1(7-37)OH are described in examples 8 and Table 9. Examples of GLP-1 analogs that have been shown to have a markedly increased GLP-1 receptor activation are described in Example 9 and Tables 8 and 9. Preferably the GLP-1 analogs of the present invention are described in Table 8 and Table 9.

GLP-1 compounds of the present invention also include GLP-1 derivatives. A "GLP-1 derivative" refers an amino acid sequence of naturally occurring truncated GLP-1 compounds, GLP-1 fragments, or a GLP-1 analog, but additionally having a chemical modification of one or more of its amino acid side groups, α-carbon atoms, terminal ammo group, or terminal carboxylic acid group. A chemical modification includes, but is not limited to, adding chemical moieties, creating new bonds, and removing chemical moieties. Modifications at amino acid side groups include, without limitation, acylation of lysine $\epsilon$-amino groups, N-alkylation of arginine, histidine, or lysine, alkylation of glutamic or aspartic carboxylic acid groups, and deamidation of glutamine or asparagine. Modifications of the terminal amino group include, without limitation, the des-amino, N-lower alkyl, N-di-lower alkyl, and N-acyl modifications. Modifications of the terminal carboxy group include, without limitation, the amide, lower alkyl amide, dialkyl amide, and lower allyl ester modifications. Furthermore, one or more side groups, or terminal groups, may be protected by protective groups known to the ordinarily-skilled protein chemist. The $\alpha$-carbon of an amino acid may be mono- or dimethylated. Preferred GLP-1 derivatives are described in U.S. Pat. No. 6,268,343 B1. A more preferred GLP-1 derivative is $Arg^{34}Lys^{26}$-(N-$\epsilon$-($\gamma$-Glu(N-$\alpha$-hexadecanoyl)))-GLP-1(7-37).

Preferred GLP-1 compounds that may be derivitized include GLP-1 analogs having modifications at one or more of the following positions: 8, 12, 16, 18, 19, 20, 22, 25, 27, 30, 33, and 37 and show increased potency compared with $Val^8$-GLP-1(7-37)OH.

Other preferred GLP-1 compounds that may be derivitized are analogs of Exendin-3 or Exendin-4. These GLP-1 compounds are described in WO99/07404, WO99/25727, WO99/25728, WO99/43708, WO00/66629, and US2001/0047084A1 and are herein incorporated by reference.

Representative examples of basal insulins that can be useful in the present invention are known in the art and are commercially available. An example of a basal insulin is insulin-NPH. Insulin-NPH is prepared by techniques widely accepted in the art and described U.S. Pat. No. 5,547,929 and Hagedorn, H. C., et al., (1936) *J. Am. Med. Assn.* 106, 177-180 and are herein incorporated by reference.

Another example of a basal insulin is an NPH-like preparation of a monomeric insulin analog referred to as monomeric insulin analog-NPD, more commonly known in the art as "NPL". NPL is Neutral Protamine formulation of LysB28-ProB29 wherein the formulation comprises an insulin complex comprising LysB28-ProB29 complexed with protamine and zinc in an aqueous medium. NPL is described in U.S. Pat. Nos. 5,461,031, 5,650,486, and 5,747,642.

The insulin analogs used in the present invention can be prepared by any of a variety of recognized peptide synthesis techniques including classical solution methods, solid phase methods, semi-synthetic methods, and recombinant DNA methods. Chance, et al., U.S. Pat. No. 5,514,646, issued May 7, 1996, discloses the preparation of various insulin analogs with sufficient detail to enable one skilled in the art to prepare any of the insulin analogs used in the present invention.

AspB28 protamine insulin crystals represent another basal insulin. AspB28 protamine insulin crystal formulations according to Balschmidt are described in U.S. Pat. No. 5,840,680. The formulations comprise crystals comprising AspB28, protamine, and a member selected from the group consisting of phenol, m-cresol, or a combination thereof and optionally further comprising zinc, in an aqueous medium.

Additionally, it is possible to have a basal insulin formulation that comprises different insulins that would be useful in the present invention. Brader described in WO99/32116 co-crystals comprising a derivatized insulin, an un-derivatized insulin, zinc, protamine, and a phenolic preservative that provide flexibility of control over the duration and shape of the glucodynamic response profile.

There are a number of other basal insulin formulations that can also be useful in the present invention. These formulations include but are not limited to insulin zinc suspensions (Ultralente (UL) and Semilente insulins) and protamine zinc insulin (PZI). Preparation of these basal insulins are well known in the art and described by Brange, in *Galenics of Insulin: The Physico-chemical and Pharmaceutical Aspects of Insulin and Insulin Preparation*, Springer-Verlag Berlin Heidelbert (1987).

Other basal insulin formulations useful in the present invention are generally described as soluble acylated basal insulins. These formulations include but are not limited to insulins acylated by fatty acids in the epsilon ($\epsilon$) amino group of LysB29.

Preparation of these basal insulins are well known in the art and described by Meyers, et al., (1997) *Diabetes* 46, 637-642, by Markussen, et al., (1996) *Diabetologia* 39, 281-288, and Havelund, et al., WO95/07931. Acylated insulins or insulin analogs are further described in U.S. Pat. No. 6,011,007. These soluble basal insulins comprise a lipophilic substituent at the $\epsilon$-amino group of the lysine at position 29 of the B chain. In one embodiment, acylated insulins analogs can have any amino acid at position 21 of the A chain except Lys, Arg and Cys, can have any amino acid at position 3 of the B chain except Lys, Arg and Cys, and can have the Phe at position 1 of the B chain present or deleted. Position 30 of the B chain can be (a) a non-codable, lipophilic amino acid having from 10 to 24 carbon atoms, in which case an acyl group of a carboxylic acid with up to 5 carbon atoms is bound to the epsilon-amino group of Lys at position 29 of the B chain, (b) any amino acid except Lys, Arg and Cys, in which case the epsilon-amino group of Lys at position 29 of the B chain has a lipophilic substituent or (c) deleted, in which case the epsilon-amino group of Lys at position 29 of the B chain has a lipophilic substituent; and any $Zn^{++}$ complexes thereof, provided that when position 30 of the B chain is Thr or Ala, positions 21 of the A chain and position 3 of the B chain are both Asn, and position 1 of the B chain is Phe, then the acylated insulin analog is a $Zn^{++}$ complex. Examples of acylated insulin analogs are described in Table 1.

TABLE 1

N$\epsilon$B29-tridecanoyl des(B30) human insulin,
N$\epsilon$B29-tetradecanoyl des(B30) human insulin,
N$\epsilon$B29-decanoyl des(B30) human insulin,
N$\epsilon$B29-dodecanoyl des(B30) human insulin,
N$\epsilon$B29-tridecanoyl GlyA21 des(B30) human insulin,
N$\epsilon$B29-tetradecanoyl GlyA21 des(B30) human insulin,
N$\epsilon$B29-decanoyl GlyA21 des(B30) human insulin,
N$\epsilon$B29-dodecanoyl GlyA21 des(B30) human insulin,
N$\epsilon$B29-tridecanoyl GlyA21 GlnB3 des(B30) human insulin,
N$\epsilon$B29-tetradecanoyl GlyA21 GlnB3 des(B30) human insulin,
N$\epsilon$B29-decanoyl GlyA21 GlnB3 des(B30) human insulin,
N$\epsilon$B29-dodecanoyl GlyA21 GlnB3 des(B30) human insulin,
N$\epsilon$B29-tridecanoyl AlaA21 des(B30) human insulin,
N$\epsilon$B29-tetradecanoyl AlaA21 des(B30) human insulin,
N$\epsilon$B29-decanoyl AlaA21 des(B30) human insulin,
N$\epsilon$B29-dodecanoyl AlaA21 des(B30) human insulin,
N$\epsilon$B29-tridecanoyl AlaA21 GlnB3 des(B30) human insulin,
N$\epsilon$B29-tetradecanoyl AlaA21 GlnB3 des(B30) human insulin,
N$\epsilon$B29-decanoyl AlaA21 GlnB3 des(B30) human insulin,
N$\epsilon$B29-dodecanoyl AlaA21 GlnB3 des(B30) human insulin,
N$\epsilon$B29-tridecanoyl GlnB3 des(B30) human insulin,
N$\epsilon$B29-tetradecanoyl GlnB3 des(B30) human insulin,
N$\epsilon$B29-decanoyl GlnB3 des(B30) human insulin,
N$\epsilon$B29-dodecanoyl GlnB3 des(B30) human insulin,
N$\epsilon$B29-tridecanoyl GlyA21 human insulin,
N$\epsilon$B29-tetradecanoyl GlyA21 human insulin,
N$\epsilon$B29-decanoyl GlyA21 human insulin, TABLE 1-continued NεB29-dodecanoyl GlyA21 human insulin,
NεB29-tridecanoyl GlyA21 GlnB3 human insulin,
NεB29-tetradecanoyl GlyA21 GlnB3 human insulin,
NεB29-decanoyl GlyA21 GlnB3 human insulin,
NεB29-dodecanoyl GlyA21 GlnB3 human insulin,
NεB29-tridecanoyl AlaA21 human insulin,
NεB29-tetradecanoyl AlaA21 human insulin,
NεB29-decanoyl AlaA21 human insulin,
NεB29-dodecanoyl AlaA21 human insulin,
NεB29-tridecanoyl AlaA21 GlnB3 human insulin,
NεB29-tetradecanoyl AlaA21 GlnB3 human insulin,
NεB29-decanoyl AlaA21 GlnB3 human insulin,
NεB29-dodecanoyl AlaA21 GlnB3 human insulin,
NεB29-tridecanoyl GlnB3 human insulin,
NεB29-tetradecanoyl GlnB3 human insulin,
NεB29-decanoyl GlnB3 human insulin,
NεB29-dodecanoyl GlnB3 human insulin,
NεB29-tridecanoyl GluB30 human insulin,
NεB29-tetradecanoyl GluB30 human insulin,
NεB29-decanoyl GluB30 human insulin,
NεB29-dodecanoyl GluB30 human insulin,
NεB29-tridecanoyl GlyA21 GluB30 human insulin,
NεB29-tetradecanoyl GlyA21 GluB30 human insulin,
NεB29-decanoyl GlyA21 GluB30 human insulin,
NεB29-dodecanoyl GlyA21 GluB30 human insulin,
NεB29-tridecanoyl GlyA21 GlnB3 GluB30 human insulin,
NεB29-tetradecanoyl GlyA21 GlnB3 GluB30 human insulin,
NεB29-decanoyl GlyA21 GlnB3 GluB30 human insulin,
NεB29-dodecanoyl GlyA21 GlnB3 GluB30 human insulin,
NεB29-tridecanoyl AlaA21 GluB30 human insulin,
NεB29-tetradecanoyl AlaA21 GluB30 human insulin,
NεB29-decanoyl AlaA21 GluB30 human insulin,
NεB29-dodecanoyl AlaA21 GluB30 human insulin,
NεB29-tridecanoyl AlaA21 GlnB3 GluB30 human insulin,
NεB29-tetradecanoyl AlaA21 GlnB3 GluB30 human insulin,
NεB29-decanoyl AlaA21 GlnB3 GluB30 human insulin,
NεB29-dodecanoyl AlaA21 GlnB3 GluB30 human insulin,
NεB29-tridecanoyl GlnB3 GluB30 human insulin,
NεB29-tetradecanoyl GlnB3 GluB30 human insulin,
NεB29-decanoyl GlnB3 GluB30 human insulin and
NεB29-dodecanoyl GlnB3 GluB30 human insulin.

Other basal insulin formulations useful in the present invention are generally described as soluble pI shifted basal insulin analogs. pI shifted analogs are described in U.S. Pat. No. 5,656,722. These analogs have pIs between about 5 and about 8.5 as a result of basic modifications to the amino acid sequence. They are stable at the weakly acid pH values of appropriate formulations even for extended periods. pI shifted analogs of human insulin have a basic modification on the C-terminal end of the B chain, a substitution of the asparagine at position 21 of the A chain, and where appropriate, a substitution of the histidine at position 10 of the B chain. Preferably, the pI shifted insulin analog has Gly at position 21 of the A chain and Arg-Arg-OH at position 31 of the B chain. Examples of pI shifted insulin analogs are described in Table 2.

TABLE 2

AspA21-Human insulin-ArgB31-OH
GluA21-Human insulin-ArgB31-OH
GlyA21-Human insulin-ArgB31-OH
SerA21-Human insulin-ArgB31-OH
ThrA21-Human insulin-ArgB31-OH
AlaA21-Human insulin-ArgB31-OH
AspA21-Human insulin-ArgB31-ArgB32-OH
GluA21-Human insulin-ArgB31-ArgB32-OH
GlyA21-Human insulin-ArgB31-ArgB32-OH
SerA21-Human insulin-ArgB31-ArgB32-OH
ThrA21-Human insulin-ArgB31-ArgB32-OH
AlaA21-Human insulin-ArgB31-ArgB32-OH
AspA21-AsnB10-Human insulin-ArgB31-OH
GluA21-AsnB10-Human insulin-ArgB31-OH TABLE 2-continued GlyA21-AsnB10-Human insulin-ArgB31-OH
SerA21-AsnB10-Human insulin-ArgB31-OH
ThrA21-AsnB10-Human insulin-ArgB31-OH
AlaA21-AsnB10-Human insulin-ArgB31-OH
AspA21-AsnB10-Human insulin-ArgB31-ArgB32-OH
GluA21-AsnB10-Human insulin-ArgB31-ArgB32-OH
GlyA21-AspB10-Human insulin-ArgB31-ArgB32-OH
SerA21-AsnB10-Human insulin-ArgB31-ArgB32-OH
ThrA21-AsnB10-Human insulin-ArgB31-ArgB32-OH
AlaA21-AsnB10-Human insulin-ArgB31-ArgB32-OH Other soluble pI shifted basal insulin analogs useful in the present invention are described in Markussen, et al., *Protein Eng.* (1988) 2:157. A preferred analog described by Markussen, et al. is GlyA21ArgB27ThrB30-NH$_2$. This analog is generally known as NovoSol Basal.

In another embodiment, the pI shifted insulin analog is human insulin with Arg at position 0 of the A chain, and Arg attached to the epsilon amino group of the Lys at position 29 of the B chain (A0$^{Arg}$-B29$^{Lys-N\epsilon-Arg}$). In another embodiment, the pI shifted insulin analog is human insulin with Arg at position 0 of the A chain, any amino acid substituted for Asn at position 21 of the A chain, and Arg attached to the epsilon amino group of the Lys at position 29 of the B chain (A0$^{Arg}$-A21$^{Xaa}$-B29$^{Lys-N\epsilon-Arg}$). In another embodiment, the pI shifted insulin analog is human insulin with Arg at position 0 of the A chain, Arg at position 0 of the B chain, and Arg attached to the epsilon amino group of the Lys at position 29 of the B chain (A0$^{Arg}$-B0$^{Arg}$-B29$^{Lys-N\epsilon-Arg}$). In another embodiment, the pI shifted insulin analog is human insulin with Arg at position 0 of the A chain, any amino acid substituted for Asn at position 21 of the A chain, Arg at position 0 of the B chain, and Arg attached to the epsilon amino group of the Lys at position 29 of the B chain (A0$^{Arg}$-A21$^{Xaa}$-B0$^{Arg}$-B29$^{Lys-N\epsilon-Arg}$). In another embodiment, the pI shifted insulin analog human insulin with Lys with Arg attached to its epsilon amino group at position at position 0 of the A chain, and Arg attached to the epsilon amino group of the Lys at position 29 of the B chain (A0$^{Lys-N\epsilon-Arg}$-B29$^{Lys-N\epsilon-Arg}$. In another embodiment, the pI shifted insulin analog human insulin with Lys with Arg attached to its epsilon amino group at position at position 0 of the A chain, any amino acid substituted for Asn at position 21 of the A chain, and Arg attached to the epsilon amino group of the Lys at position 29 of the B chain (A0$^{Lys-N\epsilon-Arg}$-A21$^{Xaa}$-B29$^{Lys-N\epsilon-Arg}$).

Other soluble pI shifted basal insulin analogs are described in United States Provisional application by Beals et al. entitled Insulin Molecule Having Protracted Time Action, filed on Aug. 2, 2002, at the United States Patent and Trademark Office. Examples of these pI shifted basal insulin analogs are described in Table 3.

TABLE 3

A0$^{Arg}$B0$^{Arg}$-insulin;
A0$^{Arg}$B0$^{Arg}$A21$^{Xaa}$-insulin;
A0$^{Arg}$B0$^{Arg}$A21$^{Gly}$-insulin;
A0$^{Arg}$B0$^{Arg}$A21$^{Ser}$-insulin;
A0$^{Lys}$B0$^{Lys}$-insulin;
A0$^{Lys}$B0$^{Lys}$A21$^{Xaa}$-insulin;
A0$^{Lys}$B0$^{Lys}$A21$^{Gly}$-insulin;
A0$^{Lys}$B0$^{Lys}$A21$^{Ser}$-insulin;
A0$^{Arg}$B0$^{Lys}$-insulin;
A0$^{Arg}$B0$^{Lys}$A21$^{Xaa}$-insulin;
A0$^{Arg}$B0$^{Lys}$A21$^{Gly}$-insulin;
A0$^{Arg}$B0$^{Lys}$A21$^{Ser}$-insulin;

TABLE 3-continued

A0$^{Lys}$B0$^{Arg}$-insulin;
A0$^{Lys}$B0$^{Arg}$A21$^{Xaa}$-insulin;
A0$^{Lys}$B0$^{Arg}$A21$^{Gly}$-insulin;
A0$^{Lys}$B0$^{Arg}$A21$^{Ser}$-insulin;
A0$^{Arg}$B0$^{Arg}$B28$^{Lys-Ne-Arg}$B29$^{Pro}$-insulin;
A0$^{Arg}$A21$^{Xaa}$B28$^{Lys-Ne-Arg}$B29$^{Pro}$-insulin;
A0$^{Arg}$A21$^{Gly}$B28$^{Lys-Ne-Arg}$B29$^{Pro}$-insulin;
A0$^{Arg}$A21$^{Gly}$B28$^{Lys-Ne-Arg}$B29$^{Pro}$-insulin;
A0$^{Arg}$B29$^{Lys-Ne-Arg}$-insulin;
A0$^{Arg}$A21$^{Xaa}$B29$^{Lys-Ne-Arg}$-insulin;
A0$^{Arg}$A21$^{Gly}$B29$^{Lys-Ne-Arg}$-insulin;
A0$^{Arg}$A21$^{Ser}$B29$^{Lys-Ne-Arg}$-insulin;
A0$^{Arg}$B29$^{Lys-Ne-Lys}$-insulin;
A0$^{Arg}$A21$^{Xaa}$B29$^{Lys-Ne-Lys}$-insulin;
A0$^{Arg}$A21$^{Gly}$B29$^{Lys-Ne-Lys}$-insulin;
A0$^{Arg}$A21$^{Ser}$B29$^{Lys-Ne-Lys}$-insulin;
A-1$^{Arg}$A0$^{Lys}$A21$^{Xaa}$B29$^{Lys-Ne-Arg}$-insulin;
A-1$^{Arg}$A0$^{Lys}$A21$^{Gly}$B29$^{Lys-Ne-Arg}$-insulin;
A-1$^{Arg}$A0$^{Lys}$A21$^{Ser}$B29$^{Lys-Ne-Arg}$-insulin;
A-1$^{Arg}$A0$^{Lys}$A21$^{Xaa}$B29$^{Lys-Ne-Arg}$-insulin;
A-1$^{Arg}$A0$^{Lys}$A21$^{Gly}$B29$^{Lys-Ne-Arg}$insulin;
A-1$^{Arg}$A0$^{Lys}$A21$^{Ser}$B29$^{Lys-Ne-Arg}$-insulin;
A-1$^{Lys}$A0$^{Lys}$A21$^{Xaa}$B29$^{Lys-Ne-Arg}$-insulin;
A-1$^{Lys}$A0$^{Lys}$A21$^{Gly}$B29$^{Lys-Ne-Arg}$-insulin;
A-1$^{Lys}$A0$^{Lys}$A21$^{Ser}$B29$^{Lys-Ne-Arg}$-insulin;
A-1$^{Lys}$A0$^{Lys}$A21$^{Xaa}$B29$^{Lys-Ne-Lys}$-insulin;
A-1$^{Lys}$A0$^{Lys}$A21$^{Gly}$B29$^{Lys-Ne-Lys}$insulin;
A-1$^{Lys}$A0$^{Lys}$A21$^{Ser}$B29$^{Lys-Ne-Lys}$-insulin;
A-1$^{Arg}$A0$^{Arg}$A21$^{Xaa}$B29$^{Lys-Ne-Arg}$-insulin;
A-1$^{Arg}$A0$^{Arg}$A21$^{Gly}$B29$^{Lys-Ne-Arg}$-insulin;
A-1$^{Arg}$A0$^{Arg}$A21$^{Ser}$B29$^{Lys-Ne-Arg}$-insulin;
A-1$^{Arg}$A0$^{Arg}$A21$^{Xaa}$B29$^{Lys-Ne-Lys}$-insulin;
A-1$^{Arg}$A0$^{Arg}$A21$^{Gly}$B29$^{Lys-Ne-Lys}$insulin;
A-1$^{Arg}$A0$^{Arg}$A21$^{Ser}$B29$^{Lys-Ne-Lys}$-insulin;
A0$^{Lys-Ne-Arg}$A21$^{Xaa}$B29$^{Lys-Ne-Arg}$-insulin;
A0$^{Lys-Ne-Arg}$A21$^{Gly}$B29$^{Lys-Ne-Arg}$-insulin;
A0$^{Lys-Ne-Arg}$A21$^{Ser}$B29$^{Lys-Ne-Arg}$-insulin;
A0$^{Lys-Ne-Arg}$A21$^{Xaa}$B29$^{Lys-Ne-Lys}$-insulin;
A0$^{Lys-Ne-Arg}$A21$^{Gly}$B29$^{Lys-Ne-Lys}$insulin;
A0$^{Lys-Ne-Arg}$A21$^{Ser}$B29$^{Lys-Ne-Lys}$-insulin;
A0$^{Lys-Ne-Lys}$A21$^{Xaa}$B29$^{Lys-Ne-Arg}$-insulin;
A0$^{Lys-Ne-Lys}$A21$^{Gly}$B29$^{Lys-Ne-Arg}$-insulin;
A0$^{Lys-Ne-Lys}$A21$^{Ser}$B29$^{Lys-Ne-Arg}$-insulin;
A0$^{Lys-Ne-Lys}$A21$^{Xaa}$B29$^{Lys-Ne-Lys}$-insulin;
A0$^{Lys-Ne-Lys}$A21$^{Gly}$B29$^{Lys-Ne-Lys}$insulin;
A0$^{Lys-Ne-Lys}$A21$^{Ser}$B29$^{Lys-Ne-Arg}$-insulin;
A0$^{Arg}$B0$^{Arg}$B29$^{Lys-Ne-Arg}$-insulin;
A0$^{Arg}$A21$^{Xaa}$B0$^{Arg}$B29$^{Lys-Ne-Arg}$-insulin;
A0$^{Arg}$A21$^{Gly}$B0$^{Arg}$B29$^{Lys-Ne-Arg}$-insulin;
A0$^{Arg}$A21$^{Ser}$B0$^{Arg}$B29$^{Lys-Ne-Arg}$-insulin;
A0$^{Arg}$B0$^{Arg}$B29$^{Lys-Ne-Lys}$-insulin;
A0$^{Arg}$A21$^{Xaa}$B0$^{Arg}$B29$^{Lys-Ne-Lys}$-insulin;
A0$^{Arg}$A21$^{Gly}$B0$^{Arg}$B29$^{Lys-Ne-Lys}$-insulin;
A0$^{Arg}$A21$^{Ser}$B0$^{Arg}$B29$^{Lys-Ne-Lys}$-insulin;
A0$^{Lys}$B0$^{Lys}$B29$^{Lys-Ne-Arg}$-insulin;
A0$^{Lys}$A21$^{Xaa}$B0$^{Lys}$B29$^{Lys-Ne-Arg}$-insulin;
A0$^{Lys}$A21$^{Gly}$B0$^{Lys}$B29$^{Lys-Ne-Arg}$-insulin;
A0$^{Lys}$A21$^{Ser}$B0$^{Lys}$B29$^{Lys-Ne-Arg}$-insulin;
A0$^{Lys}$B0$^{Lys}$B29$^{Lys-Ne-Lys}$-insulin;
A0$^{Lys}$A21$^{Xaa}$B0$^{Lys}$B29$^{Lys-Ne-Lys}$-insulin;
A0$^{Lys}$A21$^{Gly}$B0$^{Lys}$B29$^{Lys-Ne-Lys}$-insulin;
A0$^{Lys}$A2$^{Ser}$B0$^{Lys}$B29$^{Lys-Ne-Lys}$-insulin;
A0$^{gHR}$B0$^{gHR}$B29$^{Lys-Ne-Arg}$-insulin;
A0$^{gHR}$A21$^{Xaa}$B0$^{gHR}$B29$^{Lys-Ne-Arg}$-insulin;
A0$^{gHR}$A21$^{Gly}$B0$^{gHR}$B29$^{Lys-Ne-Arg}$-insulin; and
A0$^{gHR}$A21$^{Ser}$B0$^{gHR}$B29$^{Lys-Ne-Arg}$-insulin.

Both GLP-1 compounds and the insulins can have an acid at the C-terminal or an amide at the C-terminal. Native GLP-1 is an amide, therefore it is preferred that the GLP-1 compounds of the present invention also be amides. Native human insulin however, is an acid, therefore, it is preferred that the insulins of the present invention also be acids.

The present invention further provides a process of preparing pre-mixed formulations by mixing a GLP-1 compound with a basal insulin. Basal insulin may be added as a solid to a solution containing a GLP-1 compound or solid GLP-1 compound may be dissolved in a suspension or solution containing basal insulin. Alternatively, both the basal insulin and the GLP-1 compound may be added in any order to a buffered solution. In one embodiment, stock solutions of the GLP-1 compound and the basal insulin be prepared separately and then added together at the desired ratio. Preferably, a 100 Unit/ml basal insulin suspension or solution is diluted with a GLP-1 stock solution such that the final pre-mixed formulation has between 30 units/ml and 70 units/ml of basal insulin. In another embodiment, solid GLP-1 compound is dissolved in a suspension or solution containing the basal insulin. Preferably, the solid GLP-1 is dissolved in a 100 Unit/ml basal insulin suspension or solution such that the 100 Unit/ml concentration of basal insulin is maintained in the mixture formulation. Preferably, the pre-mixed formulations are buffered and contain a preservative and an isotonicity agent. The GLP-1 compound and basal insulin must be mixed in such a way as to preserve their biological activity and time-action.

For example, a pre-mixed formulation containing NPH or NPL can be prepared by dissolving a GLP-1 compound in NPH or NPL diluent. The excipients and pH of the diluent may be adjusted to maintain the GLP-1 compound in solution. However, the pH or concentration of buffer or other excipients cannot be such that when the GLP-1 compound solution is added to NPH or NPL, some or all of the insulin dissolves. Thus, it is preferable that the final pH of a pre-mixed formulation comprised of NPH or NPL be between about 7 and about 8, preferably 7.2 and 7.8. Different volumes of the GLP-1 compound solution can then be added to NPH or NPL such that the desired ratio of GLP-1 compound to insulin is obtained.

The following examples are provided merely to further illustrate the preparation of the pre-mixed formulations of the invention. The scope of the invention is not construed as merely consisting of the following examples.

EXAMPLE 1

Insulinotropic Activity Determination:

A collagenase digest of pancreatic tissue is separated on a Ficoll gradient (27%, 23%, 20.5%, and 11% in Hank's balanced salt solution, pH 7.4). The islets are collected from the 20.5%/11% interface, washed and handpicked free of exocrine and other tissue under a stereomicroscope. The islets are incubated overnight in RPMI 1640 medium supplemented with 10% fetal bovine plasma and containing 11 mM glucose at 37° C. and 95% air/5% $CO_2$. The GLP-1 compound to be studied is prepared at a range of concentrations, preferably 3 nanomolar to 30 nanomolar in RPMI medium containing 10% fetal bovine plasma and 16.7 mM glucose. About 8 to 10 isolated islets are then transferred by pipette to a total volume of 250 μl of the GLP-1 compound containing medium in 96 well microtiter dishes. The islets are incubated in the presence of the GLP-1 compound at 37° C., 95% air, 5% $CO_2$ for 90 minutes. Then aliquots of islet-free medium are collected and 100 μl thereof are assayed for the amount of insulin present by radioimmunoassay using an Equate Insulin RIA Kit (Binax, Inc., Portland, Me.).

EXAMPLE 2

Preparation of Val$^8$-GLP-1 Solutions: Several Val$^8$-GLP-1 solutions were prepared to determine the conditions that maintained solubility of the Val$^8$-GLP-1 in the presence of preservative systems used for typical basal insulin formulations. The samples were analyzed by reversed-phase HPLC chromatography to determine the total protein concentrations and the soluble protein concentrations. Table 4 summarizes the data from the various $Val^8$-GLP-1 solutions.

the pH is monitored and adjusted with base. After dissolution of $Val^8$-GLP-1, the pH was adjusted to 8 with HCl. The solution was then diluted to 100 mL 2×NPH diluent lacking phate buffer (3.2 mg/mL m-cresol, 1.30 mg/mL phenol and 32 mg/mL glycerin, pH 7.4) for a final $Val^8$-GLP-1 concen-

TABLE 4

| Buffer | Physical Appearance | pH | Theoretical $Val^8$-GLP-1 Conc. (mg/mL) | Total Protein Conc. (mg/mL) | Soluble Protein Conc. (mg/mL) | Purity (%) |
|---|---|---|---|---|---|---|
| 20 mM TRIS | clear | 7.4 | 0.5 | 0.5 | 0.49 | 92.0 |
| No Buffer | clear | 7.7 | 0.5 | 0.42 | — | 92.1 |
| 14 mM phosphate | clear | 7.8 | 1.0 | 0.99 | — | 93.0 |
| No Buffer | clear | 7.8 | 0.5 | 0.43 | — | 91.9 |
| No Buffer | clear | 7.8 | 1.25 | 0.92 | — | N/A |
| No Buffer | clear | 7.8 | 1.60 | 1.3 ave | — | 94.06 ave |
| No Buffer | clear | 7.8 | 1.60 | 1.5 | — | N/A |
| 14 mM phosphate | clear | 8.0 | 0.5 | 0.51 | — | 92.9 |
| 14 mM phosphate | clear | 8.1 | 1.0 | 0.94 | — | 91.9 |
| No Buffer | Cloudy | 7.8 | 2.50 | 2.19 | — | N/A |
| No Buffer | Cloudy | 7.8 | 5.0 | 4.01 | — | N/A |
| 14 mM phosphate | Cloudy | 7.4 | 1.0 | 0.96 | — | 96.8 |
| 7 mM phosphate | Cloudy | 7.4 | 1.0 | 0.87 | 0.91 | 93.4 |
| 20 mM TRIS | Cloudy | 7.4 | 1.0 | 0.81 | 0.91 | 93.4 |
| 20 mM TRIS | Cloudy | 7.4 | 1.0 | 1.37 | 0.81 | 93.4 |

EXAMPLE 3

Insulin Complex:

Human insulin-NPH is prepared according to accepted practice as taught by Krayenbiuhl and Rosenberg *Crystalline Protamine Insulin* 60-73, (1951). Alternatively, human insulin-NPH is commercially available in a suspension formulation under the name of Humulin-N™, manufactured by Eli Lilly and Company, Indianapolis, Ind. The unit dose and concentration of NPH used as the stock supply in these experiments was U100 at 3.5 mg/mL. The pH of comnnercial vials of NPH was adjusted to 7.2-8.5 with HCl or NaOH. The samples were analyzed by reversed-phase HPLC chromatography to determine the soluble protein concentrations. Table 5 summarizes the data from the various NPH suspensions tration of 1.6 mg/mL. The pH was adjusted to 7.8 with HCl or NaOH. The $Val^8$-GLP-1 solution was mixed with commercial insulin-NPH suspension (U100, 3.5 mg/mL) at ratios of 30:70, 50:50, and 70:30 (volume:volume) $Val^8$-GLP-1:NPH. The $Val^8$-GLP-1:NPH mixture contained final concentrations of 1.6 mg/mL m-cresol, 0.65 mg/mL phenol, 10 mM, 7 mM, and 4 mLM phosphate buffer for 30:70, 50:50, and 70:30 ratios, respectively, and 16 mg/mL glycerin. The pH was adjusted to a final pH of 7.8 with HCl or NaOH. The samples were analyzed by reversed-phase HPLC chromatography to determine the total protein concentrations and the soluble protein concentrations. Table 6 summarizes the data from the various $Val^8$-GLP-1/NPH mixtures.

TABLE 5

| Sample No. | PH | Soluble Protein Conc. (mg/mL) |
|---|---|---|
| 1 | 7.2 | 0.33 |
| 2 | 7.2 | 0.004 |
| 3 | 7.8 | 0.01 |
| 4 | 8.0 | 0.06 |
| 5 | 8.0 | 0.14 |
| 6 | 8.5 | 0.39 |
| 7 | 8.5 | 0.87 |

EXAMPLE 4

$Val^8$GLP-1/NPH Mixtures:

A solution of $Val^8$-GLP-1 was prepared by dissolving 160 mg $Val^8$-GLP-1 in 50 mL water while keeping the pH in the range of 10 to 10.5. The $Val^8$-GLP-1 is added in aliquots and

TABLE 6

| $Val^8$-GLP-1/ NPH Ratio | Theoretical Concentration (mg/mL) | | Total Protein Conc. (mg/mL) | | Soluble Protein Conc. (mg/mL) | |
|---|---|---|---|---|---|---|
| | $Val^8$-GLP-1 | Insulin | $Val^8$-GLP-1 | Insulin | $Val^8$-GLP-1 | Insulin |
| 30:70 | 0.48 | 2.45 | 0.45 | 2.44 | 0.02 | 0.11 |
| 30:70 | 0.48 | 2.45 | 0.29 | 2.30 | 0.01 | 0.07 |
| 30:70 | 0.48 | 2.45 | 0.30 | 2.26 | 0.01 | 0.14 |
| 50:50 | 0.8 | 1.75 | 0.53 | 1.71 | 0.06 | 0.41 |
| 50:50 | 0.8 | 1.75 | 0.51 | 1.67 | 0.03 | 0.48 |
| 50:50 | 0.8 | 1.75 | 0.50 | 1.68 | 0.03 | 0.41 |
| 70:30 | 1.12 | 1.05 | 0.92 | 1.09 | 0.15 | 0.68 |
| 70:30 | 1.12 | 1.05 | 0.92 | 1.04 | 0.09 | 0.86 |
| 70:30 | 1.12 | 1.05 | 0.71 | 1.06 | 0.13 | 0.73 |

The low soluble protein concentrations of $Val^8$-GLP-1 suggest that the $Val^8$-GLP-1 interacts with the NPH. However, despite adherence of the GLP-1 to the NPH crystals, the insulinotropic activity of Val$^8$-GLP-1 is not affected. See FIG. 4.

EXAMPLE 5

Exendin-4/NPH Mixtures:

A solution of Exendin-4 was prepared by dissolving 20 mg Exendin-4 in 5 mL water. The pH was adjusted to 7.4 or 7.6 with HCl or NaOH. The solution was then diluted to 10 mL 2×NPH diluent lacking phosphate buffer (3.2 mg/mL m-cresol, 1.30 mg/mL phenol and 32 mg/mL glycerin, pH 7.4) for a final Exendin-4 concentration of 2.0 mg/mL. The pH was adjusted to 7.4 with HCl or NaOH. The Exendin-4 solution was mixed with commercial insulin-NPH suspension (U100, 3.5 mg/mL) at ratios of 30:70, 50:50, and 70:30 (volume:volume) Exendin-4:NPH. The Exendin-4:NPH mixture contained final concentration of 1.6 mg/mL m-cresol, 0.65 mg/mL phenol, 10 mM, 7 mM, and 4 mM phosphate buffer for 30:70, 50:50, and 70:30 ratios, respectively, and 16 mg/mL glycerin.

The pH was adjusted to a final pH of 7.6 with HCl or NaOH. The samples were analyzed by reversed-phase HPLC chromatography to determine the total protein concentrations and the soluble protein concentrations. Table 7 summarizes the data from the various Exendin-4/NPH mixtures.

TABLE 7

| Exendin-4/ NPH Ratio | Measured pH | Theoretical Concentration (mg/mL) | | Total Protein Conc. (mg/mL) | | Soluble Protein Conc. (mg/mL) | |
|---|---|---|---|---|---|---|---|
| | | Exendin-4 | Insulin | Exendin-4 | Insulin | Exendin-4 | Insulin |
| 30:70 | 7.53 | 0.61 | 2.45 | 0.76 | 2.38 | 0.68 | 0.02 |
| 50:50 | 7.59 | 1.02 | 1.75 | 1.28 | 1.74 | 1.14 | 0.03 |
| 70:30 | 7.56 | 1.42 | 1.05 | 1.77 | 1.04 | 1.54 | 0.04 |

EXAMPLE 6

Exendin-4/Lantus® Mixtures:

A solution of Exendin-4 is prepared by dissolving 10 mg Exendin-4 in 5 mL water. The pH is adjusted to 4 with HCl. The solution is then diluted with 5 mL 2× diluent (5.4 mg/mL m-cresol, 2.5 mg/mL NaAcetate and 32 mg/mL mannitol) for a final Exendin-4 concentration of 1.0 mg/mL. The pH is adjusted to 4 with HCl. The Exendin-4 solution is mixed with commercial Lantus® insulin (U100, 3.6378 mg/mL) at ratios of 30:70, 50:50, and 70:30 (volume:volume) Exendin-4:Lantus®. The 30:70 mixture of Exendin-4:Lantus® contains final concentrations of 0.3 mg/mL Exendin-4, 70IU Lantus®, 2.7 mg/mL m-cresol, 0.75 mg/mL NaAcetate, 9.6 mg/mL mannitol, 21 µg/ml zinc, and 11.9 mg/ml glycerol. The pH is adjusted to a final pH of 4 with HCl or NaOH. The 50:50 mixture of Exendin-4:Lantus® contains final concentrations of 0.5 mg/mL Exendin-4, 50IU Lantus®, 2.7 mg/mL m-cresol, 1.25 mg/mL NaAcetate, 16 mg/mL mannitol, 15 µg/ml zinc, and 8.5 mg/ml glycerol. The pH is adjusted to a final pH of 4 with HCl or NaOH. The 70:30 mixture of Exendin-4:Lantus® contains final concentrations of 0.7 mg/mL Exendin-4, 30IU Lantus®, 2.7 mg/mL m-cresol, 1.75 mg/mL NaAcetate, 22.4 mg/mL mannitol, 9 µg/ml zinc, and 5.1 mg/ml glycerol. The pH is adjusted to a final pH of 4 with HCl or NaOH.

EXAMPLE 7

Val$^8$-Glu$^{22}$-GLP-1(7-37)OH/Lantus® Mixtures:

A solution of Val$^8$-Glu$^{22}$-GLP-1(7-37)OH is prepared by dissolving 5 mg Val$^8$-Glu$^{22}$-GLP-1(7-37)OH in 5 mL water. The pH is adjusted to 4 with HCl. The solution is then diluted with 5 mL 2× diluent (5.4 mg/mL m-cresol, 2.5 mg/mL NaAcetate and 32 mg/mL mannitol) for a final Val$^8$-Glu$^{22}$-GLP-1(7-37)OH concentration of 0.5 mg/mL. The pH is adjusted to 4 with HCl. The Val$^8$-Glu$^{22}$-GLP-1(7-37)OH solution is mixed with commercial Lantus® insulin (U00, 3.6378 mg/mL) at ratios of 30:70, 50:50, and 70:30 (volume:volume) Val$^8$-Glu$^{22}$-GLP-1(7-37)OH:Lantus®. The 30:70 mixture of Val$^8$-Glu$^{22}$-GLP-1(7-37)OH:Lantus® contains final concentrations of 0.15 mg/mL Val$^8$-Glu$^{22}$-GLP-1(7-37)OH, 70IU Lantus®, 2.7 mg/mL m-cresol, 0.75 mg/mL NaAcetate, 9.6 mg/mL mannitol, 21 µg/ml zinc, and 11.9 mg/ml glycerol. The pH is adjusted to a final pH of 4 with HCl or NaOH. The 50:50 mixture of Val$^8$-Glu$^{22}$-GLP-1(7-37)OH:Lantus® contains final concentrations of 0.25 mg/mL Val$^8$-Glu$^{22}$-GLP-1(7-37)OH, 50IU Lantus®, 2.7 mg/mL m-cresol, 1.25 mg/mL NaAcetate, 16 mg/mL mannitol, 15 µg/ml zinc, and 8.5 mg/ml glycerol. The pH is adjusted to a final pH of 4 with HCl or NaOH. The 70:30 mixture of Val$^8$-Glu$^{22}$-GLP-1(7-37)OH:Lantus® contains final concentrations of 0.35 mg/mL Val$^8$-Glu$^{22}$-GLP-1(7-37)OH, 30IU Lantus®, 2.7 mg/mL m-cresol, 1.75 mg/mL NaAcetate, 22.4 mg/mL mannitol, 9 µg/ml zinc, and 5.1 mg/ml glycerol. The pH is adjusted to a final pH of 4 with HCl or NaOH.

EXAMPLE 8

GLP Aggregation Assay:

GLP peptides can be analyzed with respect to their potential to aggregate in solution.

In general, peptides in solution are stirred at elevated temperature in a suitable buffer while recording turbidity at 350 nm as a function of time. Time to the onset of aggregation is measured to quantify the potential of a given GLP molecule to aggregate under these stressed conditions.

A GLP-1 compound is first dissolved under alkaline conditions (pH 10.5) for 30 minutes to dissolve any pre-aggregated material. The solution is then adjusted to pH 7.4 and filtered. Specifically, 4 mg of a lyophilized GLP-1 compound is dissolved in 3 ml of 10 mM phosphate/10 mM citrate. The pH is adjusted to 10.0-10.5 and held for 30 minutes. The solution is adjusted with HCl to pH 7.4 and filtered through a suitable filter, for example a Millex GV syringe filter (Millipore Corporation, Bedford, Mass.). This solution is then diluted to a final sample containing 0.3 mg/mL protein in 10 mM citrate, 10 mM phosphate, 150 mM NaCl, and adjusted to pH 7.4 to 7.5. The sample is incubated at 37° C. in a quartz cuvette. Every five minutes the turbidity of the solution is measured at 350 nm on an AVIV Model 14DS UV-VIS spectrophotometer (Lakewood, N.J.). For 30 seconds prior to and during the measurement the solution is stirred using a magnetic stir bar from Stama Cells, Inc. (Atascadero, Calif.). An increase in OD at 350 nm indicates aggregation of the GLP-peptide. The time to aggregation is approximated by the intersection of linear fits to the pre-growth and growth phase according to method of Drake(Arvinte T, Cudd A, and Drake A F.(1993) *J. Bio. Chem.* 268, 6415-6422).

The cuvette is cleaned between experiments with a caustic soap solution (e.g., Contrad-70).

The results for a number of GLP-1 compounds are reported in Table 8 as the time in hours required for the compound to aggregate. As can be seen, these compounds show greatly increased aggregation times over other GLP-1 compounds.

EXAMPLE 9

GLP-1 Receptor Activation:

The ability of the GLP-1 compounds of the present invention to activate the GLP-1 receptor was assessed using in vitro assays such as those described in EP 619,322 to Gelfand, et al., and U.S. Pat. No. 5,120,712, respectively. The entire teachings of these references are incorporated herein by reference.

In vitro potency is the measure of the ability of a peptide to activate the GLP-1 receptor in a cell-based assay. In vitro potency is expressed as the "$EC_{50}$" which is the effective concentration of compound that results in 50% activity in a single dose-response experiment. For the purposes of the present invention, in vitro potency is determined using a fluorescence assay that employs HEK-293 Aurora CRE-BLAM cells that stably express the human GLP-1 receptor. These HEK-293 cells have stably integrated a DNA vector having a cAmp response element (CRE) driving expression of the β-lactamase (BLAM) gene. The interaction of a GLP-1 agonist with the receptor initiates a signal that results in activation of the cAmp response element and subsequent expression of β-lactamase. The β-lactamase CCF2/AM substrate that emits fluorescence when it is cleaved by β-lactamase (Aurora Biosciences Corp.) can then be added to cells that have been exposed to a specific amount of GLP-1 agonist to provide a measure of GLP-1 agonist potency. The assay is further described in Zlokarnik, et al., (1998) *Science* 279:84-88 (See also Example 1). The $EC_{50}$ values were determined using the BLAM assay described above by generating a dose response curve using dilutions ranging from 0.00003 nanomolar to 30 nanomolar. Relative in vitro potency values are established by running GLP-1(7-37)OH or $Val^8$-GLP-1(7-37)OH as a control and assigning the control a reference value of 1.

The activity of these polypeptides relative to the activity of GLP-1(7-37)OH or $Val^8$-GLP-1(7-37)OH is reported in Tables 8 and 9.

TABLE 8

| GLP-1 Polypeptide | GLP-1 Receptor Activation (relative to GLP-1(7-37)OH) |
|---|---|
| GLP-1(7-37)OH | 1.0 |
| $Val^8$-GLP-1(7-37)OH | 0.47 |
| $Gly^8$-$His^{11}$-GLP-1(7-37)OH | 0.282 |
| $Val^8$-$Ala^{11}$-GLP-1(7-37)OH | 0.021 |
| $Val^8$-$Lys^{11}$-GLP-1(7-37)OH | 0.001 |
| $Val^8$-$Tyr^{12}$-GLP-1(7-37)OH | 0.81 |
| $Val^8$-$Glu^{16}$-GLP-1(7-37)OH | 0.047 |
| $Val^8$-$Ala^{16}$-GLP-1(7-37)OH | 0.112 |
| $Val^8$-$Tyr^{16}$-GLP-1(7-37)OH | 1.175 |
| $Val^8$-$Lys^{20}$-GLP-1(7-37)OH | 0.33 |
| $Gln^{22}$-GLP-1(7-37)OH | 0.42 |
| $Val^8$-$Ala^{22}$-GLP-1(7-37)OH | 0.56 |
| $Val^8$-$Ser^{22}$-GLP-1(7-37)OH | 0.50 |
| $Val^8$-$Asp^{22}$-GLP-1(7-37)OH | 0.40 |
| $Val^8$-$Glu^{22}$-GLP-1(7-37)OH | 1.29 |
| $Val^8$-$Lys^{22}$-GLP-1(7-37)OH | 0.58 |
| $Val^8$-$Pro^{22}$-GLP-1(7-37)OH | 0.01 |
| $Val^8$-$His^{22}$-GLP-1(7-37)OH | 0.14 |
| $Val^8$-$Lys^{22}$-GLP-1(7-36)$NH_2$ | 0.53 |
| $Val^8$-$Glu^{22}$-GLP-1(7-36)$NH_2$ | 1.0 |
| $Gly^8$-$Glu^{22}$-GLP-1(7-37)OH | 1.07 |
| $Val^8$-$Lys^{23}$-GLP-1(7-37)OH | 0.18 |
| $Val^8$-$His^{24}$-GLP-1(7-37)OH | 0.007 |
| $Val^8$-$Lys^{24}$-GLP-1(7-37)OH | 0.02 |
| $Val^8$-$His^{26}$-GLP-1(7-37)OH | 1.6 |
| $Val^8$-$Glu^{26}$-GLP-1(7-37)OH | 1.5 |
| $Val^8$-$His^{27}$-GLP-1(7-37)OH | 0.37 |
| $Val^8$-$Ala^{27}$-GLP-1(7-37)OH | 0.47 |
| $Gly^8$-$Glu^{30}$-GLP-1(7-37)OH | 0.29 |
| $Val^8$-$Glu^{30}$-GLP-1(7-37)OH | 0.29 |
| $Val^8$-$Asp^{30}$-GLP-1(7-37)OH | 0.15 |
| $Val^8$-$Ser^{30}$-GLP-1(7-37)OH | 0.19 |
| $Val^8$-$His^{30}$-GLP-1(7-37)OH | 0.19 |
| $Val^8$-$Glu^{33}$-GLP-1(7-37)OH | 0.039 |
| $Val^8$-$Ala^{33}$-GLP-1(7-37)OH | 0.1 |
| $Val^8$-$Gly^{33}$-GLP-1(7-37)OH | 0.01 |
| $Val^8$-$Glu^{34}$-GLP-1(7-37)OH | 0.17 |
| $Val^8$-$Pro^{35}$-GLP-1(7-37)OH | 0.094 |
| $Val^8$-$His^{35}$-GLP-1(7-37)OH | 0.41 |
| $Val^8$-$Glu^{35}$-GLP-1(7-37)OH | 0.15 |
| $Val^8$-$Glu^{36}$-GLP-1(7-37)OH | 0.11 |
| $Val^8$-$His^{36}$-GLP-1(7-37)OH | 0.22 |
| $Val^8$-$His^{37}$-GLP-1(7-37)OH | 0.33 |
| $Val^8$-$Leu^{16}$-$Glu^{26}$-GLP-1(7-37)OH | 0.23 |
| $Val^8$-$Lys^{22}$-$Glu^{30}$-GLP-1(7-37)OH | 0.37 |
| $Val^8$-$Lys^{22}$-$Glu^{23}$-GLP-1(7-37)OH | 0.35 |
| $Val^8$-$Glu^{22}$-$Ala^{27}$-GLP-1(7-37)OH | 1.02 |
| $Val^8$-$Glu^{22}$-$Lys^{23}$-GLP-1(7-37)OH | 1.43 |
| $Val^8$-$Lys^{33}$-$Val^{34}$-GLP-1(7-37)OH | 0.08 |
| $Val^8$-$Lys^{33}$-$Asn^{34}$-GLP-1(7-37)OH | 0.09 |
| $Val^8$-$Gly^{34}$-$Lys^{35}$-GLP-1(7-37)OH | 0.34 |
| $Val^8$-$Gly^{36}$-$Pro^{37}$-GLP-1(7-37)$NH_2$ | 0.53 |

TABLE 9

| Polypeptide | GLP-1 receptor activation relative to $Val^8$-GLP-1(7-37)OH |
|---|---|
| GLP-1(7-37)OH | 2.1 |
| $Val^8$-GLP-1(7-37)OH | 1.0 |
| $Gly^8$-GLP-1(7-37)OH | 1.7 |
| $Val^8$-$Tyr^{12}$-GLP-1(7-37)OH | 1.7 |
| $Val^8$-$Tyr^{12}$-GLP-1(7-36)$NH_2$ | 1.1 |
| $Val^8$-$Trp^{12}$-GLP-1(7-37)OH | 1.1 |
| $Val^8$-$Leu^{16}$-GLP-1(7-37)OH | 1.1 |
| $Val^8$-$Val^{16}$-GLP-1(7-37)OH | 1.1 |
| $Val^8$-$Tyr^{16}$-GLP-1(7-37)OH | 2.5 |
| $Gly^8$-$Glu^{22}$-GLP-1(7-37)OH | 2.2 |
| $Val^8$-$Leu^{25}$-GLP-1(7-37)OH | 0.5 |
| $Val^8$-$Tyr^{12}$-$Tyr^{16}$-GLP-1(7-37)OH | 1.5 |
| $Val^8$-$Trp^{12}$-$Glu^{22}$-GLP-1(7-37)OH | 1.7 |

TABLE 9-continued

| Polypeptide | GLP-1 receptor activation relative to Val$^8$-GLP-1(7-37)OH |
|---|---|
| Val$^8$-Tyr$^{12}$-Glu$^{22}$-GLP-1(7-37)OH | 2.7 |
| Val$^8$-Tyr$^{16}$-Phe$^{19}$-GLP-1(7-37)OH | 2.8 |
| Val$^8$-Tyr$^{16}$-Glu$^{22}$-GLP-1(7-37)OH | 3.6, 3.8 |
| Val$^8$-Trp$^{16}$-Glu$^{22}$-GLP-1(7-37)OH | 4.9, 4.6 |
| Val$^8$-Leu$^{16}$-Glu$^{22}$-GLP-1(7-37)OH | 4.3 |
| Val$^8$-Ile$^{16}$-Glu$^{22}$-GLP-1(7-37)OH | 3.3 |
| Val$^8$-Phe$^{16}$-Glu$^{22}$-GLP-1(7-37)OH | 2.3 |
| Val$^8$-Trp$^{18}$-Glu$^{22}$-GLP-1(7-37)OH | 3.2, 6.6 |
| Val$^8$-Tyr$^{18}$-Glu$^{22}$-GLP-1(7-37)OH | 5.1, 5.9 |
| Val$^8$-Phe$^{18}$-Glu$^{22}$-GLP-1(7-37)OH | 2.0 |
| Val$^8$-Ile$^{18}$-Glu$^{22}$-GLP-1(7-37)OH | 4.0 |
| Val$^8$-Lys$^{18}$-Glu$^{22}$-GLP-1(7-37)OH | 2.5 |
| Val$^8$-Trp$^{19}$-Glu$^{22}$-GLP-1(7-37)OH | 3.2 |
| Val$^8$-Phe$^{19}$-Glu$^{22}$-GLP-1(7-37)OH | 1.5 |
| Val$^8$-Phe$^{20}$-Glu$^{22}$-GLP-1(7-37)OH | 2.7 |
| Val$^8$-Glu$^{22}$-Leu$^{25}$-GLP-1(7-37)OH | 2.8 |
| Val$^8$-Glu$^{22}$-Ile$^{25}$-GLP-1(7-37)OH | 3.1 |
| Val$^8$-Glu$^{22}$-Val$^{25}$-GLP-1(7-37)OH | 4.7, 2.9 |
| Val$^8$-Glu$^{22}$-Ile$^{27}$-GLP-1(7-37)OH | 2.0 |
| Val$^8$-Glu$^{22}$-Ala$^{27}$-GLP-1(7-37)OH | 2.2 |
| Val$^8$-Glu$^{22}$-Ile$^{33}$-GLP-1(7-37)OH | 4.7, 3.8, 3.4 |
| Val$^8$-Asp$^9$-Ile$^{11}$-Tyr$^{16}$-Glu$^{22}$-GLP-1(7-37)OH | 4.3 |
| Val$^8$-Tyr$^{16}$-Trp$^{19}$-Glu$^{22}$-GLP-1(7-37)OH | 3.5 |
| Val$^8$-Trp$^{16}$-Glu$^{22}$-Val$^{25}$-Ile$^{33}$-GLP-1(7-37)OH | 5.0 |
| Val$^8$-Trp$^{16}$-Glu$^{22}$-Ile$^{33}$-GLP-1(7-37)OH | 4.1 |
| Val$^8$-Glu$^{22}$-Val$^{25}$-Ile$^{33}$-GLP-1(7-37)OH | 4.9, 5.8, 6.7 |
| Val$^8$-Trp$^{16}$-Glu$^{22}$-Val$^{25}$-GLP-1(7-37)OH | 4.4 |
| Val$^8$-Cys$^{16}$-Lys$^{26}$-GLP-1(7-37)OH | 4.2 |
| Val$^8$-Cys$^{16}$-Lys$^{26}$-Arg$^{34}$-GLP-1(7-37)OH | 2.4, 1.9 |

EXAMPLE 10

In Vivo Comparison Dog Studies:

Sample 1: A 30:70 Val$^8$-GLP-1:NPH mixture was prepared as described in example 4. The mixture contained final concentrations of 0.48 mg/ml Val$^8$-GLP-1, 2.45 mg/ml insulin-NPH, 1.6 mg/mL m-cresol, 0.65 mg/mL phenol, 10 mM phosphate buffer, and 16 mg/mL glycerin. The pH was adjusted to a final pH of 7.8.

Sample 2: A U70 suspension of commercial insulin-NPH was prepared by diluting U100 commercial insulin-NPH 30% with 1×NPH diluent. The U70 suspension of commercial insulin-NPH contained final concentrations of 2.45 mg/ml insulin-NPH, 1.6 mg/mL m-cresol, 0.65 mg/mL phenol, 14 mM phosphate buffer, and 16 mg/mL glycerin. The pH was 7.4.

Sample 3: A solution of Val$^8$-GLP-1 was prepared as described in example 4, but instead of mixing with commercial insulin-NPH suspension, the Val$^8$-GLP-1 solution was mixed with: 1×NPH diluent at a ratio of 30:70 (volume:volume) Val$^8$-GLP-1:diluent. The 30% Val$^8$-GLP-1 solution contained final concentrations of 0.48 mg/ml Val$^8$-GLP-1, 1.6 mg/mL m-cresol, 0.65 mg/mL phenol, 10 mM phosphate buffer, and 16 mg/mL glycerin. The pH was adjusted to a final pH of 7.8.

A three arm pilot study was performed in dogs comparing the above samples. In the first arm of the pilot study, sample 1 was injected into a single site on the neck of four different dogs at a dose of 0.74 U/kg NPH (1.5 nmol/kg Val$^8$-GLP-1). A 3-hour hyperglycemic (150 mg/dl) clamp was initiated and glucose infusion rates were continually recorded. Blood samples were taken periodically for the determination of plasma glucose, insulin, C-peptide, and immunoreactive GLP-1 concentrations. Plasma glucose concentrations were determined on the day of study. The remainder of the samples were then frozen (−80° C.) and assayed for hormone concentration determinations at a later time.

In the second arm of the pilot study, sample 2 was injected into one site on the neck of the same four dogs at a dose of 0.74 U/kg NPH. Also at the same time, sample 3 was injected into a second site on the neck of the same four dogs at a dose of 1.5 mmol/kg Val$^8$-GLP-1. Again, a 3-hour hyperglycemic (150 mg/dl) clamp was initiated and glucose infusion rates were continually recorded. Blood samples were taken periodically for the determination of plasma glucose, insulin, C-peptide, and immunoreactive GLP-1 concentrations. Plasma glucose concentrations were determined on the day of study. The remainder of the samples were then frozen (−80° C.) and assayed for hormone concentration determinations at a later time.

In the third arm of the pilot study, sample 2 only was injected into a single site on the neck of the same four dogs at a dose of 0.74 U/kg NPH. Again, a 3-hour hyperglycemic (150 mg/dl) clamp was initiated and glucose infusion rates were continually recorded. Blood samples were taken periodically for the determination of plasma glucose, insulin, C-peptide, and immunoreactive GLP-1 concentrations. Plasma glucose concentrations were determined on the day of study. The remainder of the samples were then frozen (−80° C.) and assayed for hormone concentration determinations at a later time.

The results of the in vivo comparison dog study, shown in FIGS. 1-4, indicate that when Val$^8$-GLP-1 was injected, there was a clear increase in glucodynamic activity over that observed when only insulin-NPH was injected (see FIG. 1). Surprisingly, the increase in glucodynamic activity tended to be more robust and consistent with the first arm of the study as compared to the second arm of the study (see FIGS. 1 and 2). However, the C-peptide and immunoreactive GLP-1 concentrations of the first arm were comparable to the second arm (see FIGS. 3 and 4, respectively). Also observed was a prolongation of absorption of Val$^8$-GLP-1 in the first arm of the study as compared to the absorption of Val$^8$-GLP-1 in the second arm of the study (see FIG. 4).

EXAMPLE 11

Exendin-4/Lantus® Mixtures:

Exendin-4 (160 μg) was dissolved in 100 μL of commercial Lantus® insulin (U00, 3.6378 mg/mL). The mixture was hand swirled gently until the solids were dissolved and a clear solution was obtained. The solution was stored at 5° C. After 18 hours the solution was still clear without precipitation. The pH was 4.0 Final concentrations of Exendin-4 and Lantus® were determined by reverse phase HPLC to be 0.9 mg/mL Exendin-4 and 3.5 mg/mL Lantus®. Based on known concentrations of excipients in the commercial formulation of Lantus®, the final concentrations of excipients in the mixture were as follows: 2.7 mg/mL m-cresol, 30 μg/mL zinc, and 17 mg/ml glycerol.

EXAMPLE 12

Exendin-4/Lantus® Mixtures:

Exendin-4 (290 μg) was dissolved in 100 μL of commercial Lantus® insulin U100, 3.6378 mg/mL). The mixture was hand swirled gently until the solids were dissolved and a clear solution was obtained. The pH of the solution was adjusted to 4.0 with NaOH. Final concentrations of Exendin-4 and Lantus® were determined by reverse phase HPLC to be 1.6 mg/mL Exendin-4 and 3.5 mg/mL Lantus®. Based on known concentrations of excipients in the commercial formulation of Lantus®, the final concentrations of excipients in the mixture were as follows: 2.7 mg/mL m-cresol, 30 µg/ml zinc, and 17 mg/ml glycerol.

EXAMPLE 13

Exendin-4/Lantus® Mixtures:

Exendin-4 (529 µg) was dissolved in 500 µL of commercial Lantus® insulin (U100, 3.6378 mg/mL). The mixture was hand swirled gently until the solids were dissolved and a clear solution was obtained. The pH of the solution was adjusted to 4.0 with NaOH. Final concentrations of Exendin-4 and Lantus® were calculated to be 1 mg/mL Exendin-4 and 3.5 mg/mL Lantus®. Based on known concentrations of excipients in the commercial formulation of Lantus®, the final concentrations of excipients in the mixture were as follows: 2.7 mg/mL m-cresol, 30 µg/ml zinc, and 17 mg/ml glycerol.

EXAMPLE 14

$Val^8$-$Glu^{22}$-GLP-1(7-37)OH/Lantus® Mixtures:

A stock solution of $Val^8$-$Glu^{22}$-GLP-1(7-37)OH was prepared by dissolving 2.1 mg of $Val^8$-$Glu^{22}$-GLP-1(7-37)OH in 1 ml of 0.01 N HCl. The pH was adjusted to 11.3 with NaOH to obtain a clear solution. The pH was then adjusted to 4.0 with HCl and remained clear. $Val^8Glu^{22}$-GLP-1(7-37)OH (300 µL of stock solution) was added to 700 µL of commercial Lantus® insulin (U1100, 3.6378 mg/mL). The pH was adjusted to 3.3 with HCl to obtain a clear solution, and then adjusted to 4.2 with NaOH and the solution remained clear. Final concentrations of $Val^8$-$Glu^{22}$-GLP-1(7-37)OH and Lantus® were determined by reverse phase HPLC to be 0.5 mg/mL $Val^8$-$Glu^{22}$-GLP-1(7-37)OH and 2.4 mg/mL Lantus®. Based on known concentrations of excipients in the commercial formulation of Lantus®, the final concentrations of excipients in the mixture were as follows: 1.9 mg/mL m-cresol, 21 µg/ml zinc, and 11.9 mg/ml glycerol.

EXAMPLE 15

$Val^8$-$Glu^{22}$-GLP-1(7-37)QH/Lantus® Mixtures:

Stock solution A was prepared by dissolving 2.0 g of synthetic glycerin, 0.3 g meta-cresol, and 120 µL of a 25 mg/mL Zinc oxide solution in 100 mL of sterile water. The solution was filtered with Millipore Sterivex-GV 0.22 µm filter.

A stock solution of $Val^8$-$Glu^{22}$-GLP-1(7-37)OH was prepared by dissolving 4.8 mg of $Val^8$-$Glu^{22}$-GLP-1(7-37)OH in 1.5 ml of. Stock solution A. The pH was adjusted to 11 with NaOH. The pH was then adjusted to 4.0 with HCl and the solution remained clear. $Val^8$-$Glu^{22}$-GLP-1(7-37)OH (300 µL of stock solution) was added to 700 µL of commercial Lantus® insulin (U100, 3.6378 mg/mL). The pH was adjusted to 2.7 with HCl to obtain a clear solution, and then adjusted to 3.5 with NaOH. Final concentrations of $Val^8$-$Glu^{22}$-GLP-1(7-37)OH and Lantus® were calculated to be 0.96 mg/mL $Val^8$-$Glu^{22}$-GLP-1(7-37)OH and 2.5 mg/mL Lantus®. Based on known concentrations of excipients in the commercial formulation of Lantus®, the final concentrations of excipients in the mixture were as follows: 1.9 mg/mL m-cresol, 21 µg/ml zinc, and 11.9 mg/ml glycerol.

EXAMPLE 16

Exendin-4/$A0^{Arg}$-$B0^{Arg}$-$B29^{Lys-N\epsilon-Arg}$ Mixtures:

Stock solution A was prepared by dissolving 2.0 g of synthetic glycerin, 0.3 g meta-cresol, and 120 µL of a 25 mg/mL Zinc oxide solution in 100 mL of sterile water.

The solution was filtered with Millipore Sterivex-GV 0.22 µm filter.

$A0^{Arg}$-$B0^{Arg}$-$B29^{Lys-N\epsilon-Arg}$ (human insulin with Arg at position 0 of the A chain, Gly at position 21 of the A chain, Arg at position 0 of the B chain, and Arg attached to the epsilon amino group of the Lys at position 29 of the B chain) (384 µg) was dissolved in 100 µL of Stock solution A. The pH of the solution was adjusted to 4.0 with NaOH.

Exendin-4 (197 µg) was dissolved in the $A0^{Arg}$-$B0^{Arg}$-$B29^{Lys-N\epsilon-Arg}$ solution. The pH of the solution was adjusted to 4.1 with NaOH. Final concentrations of Exendin-4 and $A0^{Arg}$-$B0^{Arg}$-$B29^{Lys-N\epsilon-Arg}$ were determined by HPLC to be 1.1 mg/mL Exendin-4, and 2.4 mg/mL $A0^{Arg}$-$B0^{Arg}$-$B29^{Lys-N\epsilon-Arg}$.

EXAMPLE 17

Exendin-4/$A0^{Arg}$-$B0^{Arg}$-$B29^{Lys-N\epsilon-Arg}$ Mixtures:

Stock solution A was prepared by dissolving 2.0 g of synthetic glycerin, 0.3 g meta-cresol, and 120 µL of a 25 mg/mL Zinc oxide solution in 100 mL of sterile water. The solution was filtered with Millipore Sterivex-GV 0.22 µm filter.

$A0^{Arg}$-$B0^{Arg}$-$B29^{Lys-N\epsilon-Arg}$(human insulin with Arg at position 0 of the A chain, Gly at position 21 of the A chain, Arg at position 0 of the B chain, and Arg attached to the epsilon amino group of the Lys at position 29 of the B chain) (1.84 mg) was dissolved in 500 µL of Stock solution A. The pH of the solution was adjusted to 4.1 with NaOH.

Exendin-4 (568 µg) was dissolved in the $A0^{Arg}$-$B0^{Arg}$-$B29^{Lys-N\epsilon-Arg}$ solution. The pH of the solution was adjusted to 4.2 with NaOH. Final concentrations are calculated to be 1.1 mg/mL Exendin-4, and 3.68 mg/mL $A0^{Arg}$-$B0^{Arg}$-$B29^{Lys-N\epsilon-Arg}$.

We claim:

1. A pre-mixed formulation comprising a GLP-1 compound and an acylated basal insulin wherein the GLP-1 compound is $Arg^{34}Lys^{26}$-(N-ε-(γ-Glu(N-α-hexadecanoyl)))-GLP-1(7-37) and the acylated basal insulin is NεB29-tetradecanoyl des(B30) human insulin.

2. A process of preparing the pre-mixed formulation of claim 1, wherein the process comprises the steps of mixing said GLP-1 compound with said basal insulin in an aqueous medium.

3. A method of treating a condition selected from the group consisting of non-insulin dependent diabetes and insulin dependent diabetes comprising administering an effective amount of a pre-mixed formulation of claim 1 to a patient in need thereof.

* * * * *

SEQUENCE LISTING

```
<160> NUMBER OF SEQ ID NOS: 6

<210> SEQ ID NO 1
<211> LENGTH: 31
<212> TYPE: PRT
<213> ORGANISM: Homo sapiens
<220> FEATURE:
```

```
<221> NAME/KEY: MISC_FEATURE
<222> LOCATION: (31)..(31)
<223> OTHER INFORMATION: Xaa at position 31 is Gly or -NH2.

<400> SEQUENCE: 1

His Ala Glu Gly Thr Phe Thr Ser Asp Val Ser Ser Tyr Leu Glu Gly
1               5                   10                  15

Gln Ala Ala Lys Glu Phe Ile Ala Trp Leu Val Lys Gly Arg Xaa
            20                  25                  30

<210> SEQ ID NO 2
<211> LENGTH: 39
<212> TYPE: PRT
<213> ORGANISM: artificial sequence
<220> FEATURE:
<223> OTHER INFORMATION: Synthetic Construct
<220> FEATURE:
<221> NAME/KEY: MISC_FEATURE
<222> LOCATION: (2)..(2)
<223> OTHER INFORMATION: Xaa at position 2 is Ser or Gly;
<220> FEATURE:
<221> NAME/KEY: MISC_FEATURE
<222> LOCATION: (39)..(39)
<223> OTHER INFORMATION: Ser at position 39 is either Ser or Ser-NH2;
<220> FEATURE:
<221> NAME/KEY: MISC_FEATURE
<222> LOCATION: (3)..(3)
<223> OTHER INFORMATION: Xaa at 3 is Asp or Glu.

<400> SEQUENCE: 2

His Xaa Xaa Gly Thr Phe Thr Ser Asp Leu Ser Lys Gln Met Glu Glu
1               5                   10                  15

Glu Ala Val Arg Leu Phe Ile Glu Trp Leu Lys Asn Gly Gly Pro Ser
            20                  25                  30

Ser Gly Ala Pro Pro Pro Ser
        35

<210> SEQ ID NO 3
<211> LENGTH: 39
<212> TYPE: PRT
<213> ORGANISM: Artificial Sequence
<220> FEATURE:
<223> OTHER INFORMATION: Synthetic Construct
<220> FEATURE:
<221> NAME/KEY: MISC_FEATURE
<222> LOCATION: (1)..(1)
<223> OTHER INFORMATION: Xaa at position 1 is L-histidine, D-histidine,
    desamino-histidine, 2-amino-histidine, beta-hydroxy-histidine,
    homohistidine, alpha-fluoromethl-histidine or alpha-methyl-
    histidine
<220> FEATURE:
<221> NAME/KEY: MISC_FEATURE
<222> LOCATION: (2)..(2)
<223> OTHER INFORMATION: Xaa at position 2 is Ala, Gly, Ser. Thr, Leu,
    Ile, Val, Glu, Asp, or Lys;
<220> FEATURE:
<221> NAME/KEY: MISC_FEATURE
<222> LOCATION: (3)..(3)
<223> OTHER INFORMATION: Xaa at position 3 is Glu, Asp Lys, Thr, Ser,
    Arg, Trp, Phe, Tyr, or His;
<220> FEATURE:
<221> NAME/KEY: MISC_FEATURE
<222> LOCATION: (5)..(5)
<223> OTHER INFORMATION: Xaa at position 5 is Thr, Ala, Gly, Ser, Leu,
    Ile, Val, Glu, Asp, Arg, His, or Lys;
<220> FEATURE:
<221> NAME/KEY: MISC_FEATURE
<222> LOCATION: (6)..(6)
<223> OTHER INFORMATION: Xaa at position 6 is His, Trp, Phe, or Tyr;
<220> FEATURE:
<221> NAME/KEY: MISC_FEATURE
<222> LOCATION: (8)..(8)
```

-continued

```
<223> OTHER INFORMATION: Xaa at position 8 is Ser, Ala, Gly, Thr, Leu,
      Ile, Val, Glu, Asp, or Lys;
<220> FEATURE:
<221> NAME/KEY: MISC_FEATURE
<222> LOCATION: (10)..(10)
<223> OTHER INFORMATION: Xaa at position 10 is Val, Ala, Gly, Ser, Thr,
      Leu, Ile, Tyr, Glu, Asp, Trp, His, Phe, or Lys;
<220> FEATURE:
<221> NAME/KEY: MISC_FEATURE
<222> LOCATION: (11)..(11)
<223> OTHER INFORMATION: Xaa at position 11 is Ser, Ala, Gly, Thr, Leu,
      Ile, Val, Glu, Asp, or Lys;
<220> FEATURE:
<221> NAME/KEY: MISC_FEATURE
<222> LOCATION: (12)..(12)
<223> OTHER INFORMATION: Xaa at position 12 is Ser, Ala, Gly, Thr, Leu,
      Ile, Val, Glu, Asp, His, Pro, Arg, or Lys;
<220> FEATURE:
<221> NAME/KEY: MISC_FEATURE
<222> LOCATION: (13)..(13)
<223> OTHER INFORMATION: Xaa at position 13 is Tyr, Phe, Trp, Glu, Asp,
      Gly, Gln, Asn, Arg, Cys, or Lys;
<220> FEATURE:
<221> NAME/KEY: MISC_FEATURE
<222> LOCATION: (14)..(14)
<223> OTHER INFORMATION: Xaa at position 14 is Leu, Ala, Gly, Ser, Thr,
      Ile, Val, Glu, Asp, Met, or Lys;
<220> FEATURE:
<221> NAME/KEY: MISC_FEATURE
<222> LOCATION: (15)..(15)
<223> OTHER INFORMATION: Xaa at position 15 is Glu, Asp, or Lys;
<220> FEATURE:
<221> NAME/KEY: MISC_FEATURE
<222> LOCATION: (16)..(16)
<223> OTHER INFORMATION: Xaa at position 16 is Gly, Ala, Ser, Thr, Leu,
      Ile, Val, Glu, Asp, or Lys;
<220> FEATURE:
<221> NAME/KEY: MISC_FEATURE
<222> LOCATION: (17)..(17)
<223> OTHER INFORMATION: Xaa at position 17 is Gln, Asn, Arg, Glu, Asp,
      His, or Lys;
<220> FEATURE:
<221> NAME/KEY: MISC_FEATURE
<222> LOCATION: (18)..(18)
<223> OTHER INFORMATION: Xaa at position 18 is Ala, Gly, Ser, Thr, Leu,
      Ile, Val, Arg, Glu, Asp, or Lys;
<220> FEATURE:
<221> NAME/KEY: MISC_FEATURE
<222> LOCATION: (19)..(19)
<223> OTHER INFORMATION: Xaa at position 19 is Ala, Gly, Ser, Thr, Leu,
      Ile, Val, Glu, Asp, or Lys;
<220> FEATURE:
<221> NAME/KEY: MISC_FEATURE
<222> LOCATION: (20)..(20)
<223> OTHER INFORMATION: Xaa at position 20 is Lys, Arg, Gln, Glu, Asp,
      Trp, Tyr, Phe, or His;
<220> FEATURE:
<221> NAME/KEY: MISC_FEATURE
<222> LOCATION: (21)..(21)
<223> OTHER INFORMATION: Xaa at position 21 is Glu, Asp, Ala, His, Phe,
      Tyr, Trp, Arg, Leu, or Lys;
<220> FEATURE:
<221> NAME/KEY: MISC_FEATURE
<222> LOCATION: (24)..(24)
<223> OTHER INFORMATION: Xaa at position 24 is Ala, Gly, Ser, Thr, Leu,
      Ile, Val, Glu, Asp, His, or Lys;
<220> FEATURE:
<221> NAME/KEY: MISC_FEATURE
<222> LOCATION: (25)..(25)
<223> OTHER INFORMATION: Xaa at position 25 is Trp, Phe, Tyr, Glu, Asp,
      Ser, Thr, Arg, or Lys;
<220> FEATURE:
<221> NAME/KEY: MISC_FEATURE
<222> LOCATION: (26)..(26)
<223> OTHER INFORMATION: Xaa at position 26 is Leu, Gly, Ala, Ser, Thr,
      Ile, Val, Glu, Asp, or Lys;
<220> FEATURE:
<221> NAME/KEY: MISC_FEATURE
<222> LOCATION: (27)..(27)
```

```
<223> OTHER INFORMATION: Xaa at position 27 is Val, Gly, Ala, Ser, Thr,
      Leu, Ile, Glu, Asp, Arg, or Lys;
<220> FEATURE:
<221> NAME/KEY: MISC_FEATURE
<222> LOCATION: (28)..(28)
<223> OTHER INFORMATION: Xaa at position 28 is Lys, Arg, Glu, Asp, Asn,
      or His;
<220> FEATURE:
<221> NAME/KEY: MISC_FEATURE
<222> LOCATION: (29)..(29)
<223> OTHER INFORMATION: Xaa at position 29 is Gly, Ala, Ser, Thr, Leu,
      Ile, Val, Glu, Asp, Arg, Trp, Tyr, Phe, Pro, His, or Lys;
<220> FEATURE:
<221> NAME/KEY: MISC_FEATURE
<222> LOCATION: (30)..(30)
<223> OTHER INFORMATION: Xaa at position 30 is Arg, Lys, Glu, Asp, Thr,
      Ser, Trp, Tyr, Phe, Gly, or His;
<220> FEATURE:
<221> NAME/KEY: MISC_FEATURE
<222> LOCATION: (31)..(31)
<223> OTHER INFORMATION: Xaa at position 31 is Gly, Ala, Ser, Thr, Leu,
      Ile, Val, Glu, Asp, His, Lys, Arg, Trp, Tyr, Phe, Pro, Pro-NH2
      or is deleted;
<220> FEATURE:
<221> NAME/KEY: MISC_FEATURE
<222> LOCATION: (32)..(32)
<223> OTHER INFORMATION: Xaa at position 32 is Arg, Lys, Glu, Asp, Ser,
      or His, or is deleted;
<220> FEATURE:
<221> NAME/KEY: MISC_FEATURE
<222> LOCATION: (33)..(33)
<223> OTHER INFORMATION: Xaa at position 33 is Arg, Lys, Glu, Asp, Ser,
      or His, or is deleted;
<220> FEATURE:
<221> NAME/KEY: MISC_FEATURE
<222> LOCATION: (34)..(34)
<223> OTHER INFORMATION: Xaa at position 34 is Asp, Glu, Gly, or Lys, or
      is deleted;
<220> FEATURE:
<221> NAME/KEY: MISC_FEATURE
<222> LOCATION: (35)..(35)
<223> OTHER INFORMATION: Xaa at position 35 is Phe, Trp, Tyr, Glu, Asp,
      Ala, or Lys, or is deleted;
<220> FEATURE:
<221> NAME/KEY: MISC_FEATURE
<222> LOCATION: (36)..(36)
<223> OTHER INFORMATION: Xaa at position 36 is Ser, Pro, Lys, Glu, or
      Asp, or is deleted;
<220> FEATURE:
<221> NAME/KEY: MISC_FEATURE
<222> LOCATION: (37)..(37)
<223> OTHER INFORMATION: Xaa at position 37 is Ser, Glu, Asp, Pro, or
      Lys, or is deleted;
<220> FEATURE:
<221> NAME/KEY: MISC_FEATURE
<222> LOCATION: (38)..(38)
<223> OTHER INFORMATION: Xaa at position 38 is Gly, Glu, Asp, Pro, or
      Lys, or is deleted; and
<220> FEATURE:
<221> NAME/KEY: MISC_FEATURE
<222> LOCATION: (39)..(39)
<223> OTHER INFORMATION: Xaa at position 39 is Ala, Val, Glu, Asp, Ser,
      Lys, Ala-NH2, Val-NH2, Glu-NH2, Asp-NH2, Ser-NH2, Lys-NH2, or is
      deleted, or a C-1-6-ester, or amide, or C-1-6-alkylamide, or C-1-
      6-dialkylamide.

<400> SEQUENCE: 3

Xaa Xaa Xaa Gly Xaa Xaa Thr Xaa Asp Xaa Xaa Xaa Xaa Xaa Xaa Xaa
1               5                   10                  15

Xaa Xaa Xaa Xaa Xaa Phe Ile Xaa Xaa Xaa Xaa Xaa Xaa Xaa Xaa Xaa
            20                  25                  30

Xaa Xaa Xaa Xaa Xaa Xaa Xaa
        35

<210> SEQ ID NO 4
```

```
<211> LENGTH: 31
<212> TYPE: PRT
<213> ORGANISM: artificial sequence
<220> FEATURE:
<223> OTHER INFORMATION: Synthietic Construct
<220> FEATURE:
<221> NAME/KEY: MISC_FEATURE
<222> LOCATION: (2)..(2)
<223> OTHER INFORMATION: Xaa at position 2 is Gly, Ala, Val, Leu, Ile,
      Ser, or Thr;
<220> FEATURE:
<221> NAME/KEY: MISC_FEATURE
<222> LOCATION: (16)..(16)
<223> OTHER INFORMATION: Xaa at position 16 is Asp, Glu, Gln, Asn, Lys,
      Arg, Cys, or Cysteic Acid;
<220> FEATURE:
<221> NAME/KEY: MISC_FEATURE
<222> LOCATION: (17)..(17)
<223> OTHER INFORMATION: Xaa at position 17 is His, Asp, Lys, Glu, or
      Gln;
<220> FEATURE:
<221> NAME/KEY: MISC_FEATURE
<222> LOCATION: (21)..(21)
<223> OTHER INFORMATION: Xaa at position 21 is Ala, Glu, His, Phe, Tyr,
      Trp, Arg, or Lys;
<220> FEATURE:
<221> NAME/KEY: MISC_FEATURE
<222> LOCATION: (24)..(24)
<223> OTHER INFORMATION: Xaa at position 24 is Glu, Asp, Ser, or His;
<220> FEATURE:
<221> NAME/KEY: MISC_FEATURE
<222> LOCATION: (31)..(31)
<223> OTHER INFORMATION: R at position 31 is Lys, Arg, Thr, Ser, Glu,
      Asp, Trp, Tyr, Phe, His, -NH2.

<400> SEQUENCE: 4

His Xaa Glu Gly Thr Phe Thr Ser Asp Val Ser Ser Tyr Leu Glu Xaa
1               5                   10                  15

Xaa Ala Ala Lys Xaa Phe Ile Xaa Trp Leu Val Lys Gly Arg Arg
            20                  25                  30

<210> SEQ ID NO 5
<211> LENGTH: 31
<212> TYPE: PRT
<213> ORGANISM: artificial sequence
<220> FEATURE:
<223> OTHER INFORMATION: Synthetic Construct
<220> FEATURE:
<221> NAME/KEY: MISC_FEATURE
<222> LOCATION: (1)..(1)
<223> OTHER INFORMATION: Xaa at position 1 is L-histidine, D-histidine,
      desamino-histidine, 2-amino-histidine, beta-hydroxy-histidine,
      homohistidine, alpha-fluoromethyl-histidine, or alpha-methyl-
      histidine;
<220> FEATURE:
<221> NAME/KEY: MISC_FEATURE
<222> LOCATION: (2)..(2)
<223> OTHER INFORMATION: Xaa at position 2 is Ala, Gly, Val, Leu, Ile,
      Ser, or Thr;
<220> FEATURE:
<221> NAME/KEY: MISC_FEATURE
<222> LOCATION: (6)..(6)
<223> OTHER INFORMATION: Xaa at position 6 is Phe, Trp, or Tyr;
<220> FEATURE:
<221> NAME/KEY: MISC_FEATURE
<222> LOCATION: (10)..(10)
<223> OTHER INFORMATION: Xaa at position 10 is Val, Trp, Ile, Leu, Phe,
      or Tyr;
<220> FEATURE:
<221> NAME/KEY: MISC_FEATURE
<222> LOCATION: (12)..(12)
<223> OTHER INFORMATION: Xaa at position 12 is Ser, Trp, Tyr, Phe, Lys,
      Ile, Leu, Val;
<220> FEATURE:
<221> NAME/KEY: MISC_FEATURE
<222> LOCATION: (13)..(13)
```

```
<223> OTHER INFORMATION: Xaa at position 13 is Tyr, Trp, or Phe;
<220> FEATURE:
<221> NAME/KEY: MISC_FEATURE
<222> LOCATION: (14)..(14)
<223> OTHER INFORMATION: Xaa at position 14 is Leu, Phe, Tyr, or Trp;
<220> FEATURE:
<221> NAME/KEY: MISC_FEATURE
<222> LOCATION: (16)..(16)
<223> OTHER INFORMATION: Xaa at position 16 is Gly, Glu, Asp, or Lys;
<220> FEATURE:
<221> NAME/KEY: MISC_FEATURE
<222> LOCATION: (19)..(19)
<223> OTHER INFORMATION: Xaa at position 19 is Ala, Val, Ile, or Leu;
<220> FEATURE:
<221> NAME/KEY: MISC_FEATURE
<222> LOCATION: (21)..(21)
<223> OTHER INFORMATION: Xaa at position 21 is Glu, Ile, or Ala;
<220> FEATURE:
<221> NAME/KEY: MISC_FEATURE
<222> LOCATION: (24)..(24)
<223> OTHER INFORMATION: Xaa at position 24 is Ala or Glu;
<220> FEATURE:
<221> NAME/KEY: MISC_FEATURE
<222> LOCATION: (27)..(27)
<223> OTHER INFORMATION: Xaa at position 27 is Val or Ile; and
<220> FEATURE:
<221> NAME/KEY: MISC_FEATURE
<222> LOCATION: (31)..(31)
<223> OTHER INFORMATION: Xaa at position 31 is Gly, His, NH2, or is
      absent.

<400> SEQUENCE: 5

Xaa Xaa Glu Gly Thr Xaa Thr Ser Asp Xaa Ser Xaa Xaa Xaa Glu Xaa
 1               5                  10                  15

Gln Ala Xaa Lys Xaa Phe Ile Xaa Trp Leu Xaa Lys Gly Arg Xaa
             20                  25                  30

<210> SEQ ID NO 6
<211> LENGTH: 31
<212> TYPE: PRT
<213> ORGANISM: artificial sequence
<220> FEATURE:
<223> OTHER INFORMATION: Synthetic Construct
<220> FEATURE:
<221> NAME/KEY: MISC_FEATURE
<222> LOCATION: (1)..(1)
<223> OTHER INFORMATION: Xaa at position 1 is L-histidine, D-histidine,
      desamino-histidine, 2-amino-histidine, beta-hydroxy-histidine,
      homohistidine, alpha-fluoromethyl-histidine, or alpha-methyl-
      hisitidine;
<220> FEATURE:
<221> NAME/KEY: MISC_FEATURE
<222> LOCATION: (2)..(2)
<223> OTHER INFORMATION: Xaa at position 2 is Gly, Ala, Val, Leu, Ile,
      Ser, or Thr;
<220> FEATURE:
<221> NAME/KEY: MISC_FEATURE
<222> LOCATION: (10)..(10)
<223> OTHER INFORMATION: Xaa at position 10 is Val, Phe, Tyr, or Trp;
<220> FEATURE:
<221> NAME/KEY: MISC_FEATURE
<222> LOCATION: (12)..(12)
<223> OTHER INFORMATION: Xaa at position 12 is Ser, Tyr, Trp, Phe, Lys,
      Ile, Leu, or Val;
<220> FEATURE:
<221> NAME/KEY: MISC_FEATURE
<222> LOCATION: (16)..(16)
<223> OTHER INFORMATION: Xaa at position 16 is Gly, Glu, Asp, or Lys;
<220> FEATURE:
<221> NAME/KEY: MISC_FEATURE
<222> LOCATION: (19)..(19)
<223> OTHER INFORMATION: Xaa at position 19 is Ala, Val, Ile, or Leu;
<220> FEATURE:
<221> NAME/KEY: MISC_FEATURE
<222> LOCATION: (27)..(27)
<223> OTHER INFORMATION: Xaa at position 27 is Val or Ile; and
```

```
-continued

<220> FEATURE:
<221> NAME/KEY: MISC_FEATURE
<222> LOCATION: (31)..(31)
<223> OTHER INFORMATION: Xaa at position 31 is Gly, NH2, or is absent.

<400> SEQUENCE: 6

Xaa Xaa Glu Gly Thr Phe Thr Ser Asp Xaa Ser Xaa Tyr Leu Glu Xaa
1               5                   10                  15

Gln Ala Xaa Lys Glu Phe Ile Ala Trp Leu Xaa Lys Gly Arg Xaa
            20                  25              30
```